United States Patent
Enomoto

(10) Patent No.: US 11,925,504 B2
(45) Date of Patent: Mar. 12, 2024

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Jun Enomoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 213 days.

(21) Appl. No.: 17/353,435

(22) Filed: Jun. 21, 2021

(65) Prior Publication Data
US 2021/0307718 A1    Oct. 7, 2021

Related U.S. Application Data

(63) Continuation of application No. PCT/JP2019/044461, filed on Nov. 13, 2019.

(30) Foreign Application Priority Data

Dec. 27, 2018  (JP) ................ 2018-245545

(51) Int. Cl.
*A61B 8/08*   (2006.01)
*A61B 8/00*   (2006.01)

(52) U.S. Cl.
CPC .......... *A61B 8/0841* (2013.01); *A61B 8/461* (2013.01)

(58) Field of Classification Search
CPC ......... A61B 8/0841; A61B 8/461; A61B 8/14; A61B 8/5207; A61B 8/462; A61B 8/00; A61B 34/20; A61B 2034/2046; A61B 2034/2063; A61B 2576/00; A61B 17/3403; A61B 2017/3413; A61B 2090/378; A61B 17/34; A61B 2090/37; H04N 13/344
See application file for complete search history.

(56) References Cited

U.S. PATENT DOCUMENTS

| | | | |
|---|---|---|---|
| 2013/0120224 A1 | 5/2013 | Cajigas et al. | |
| 2015/0148664 A1* | 5/2015 | Stolka | A61B 34/20 600/440 |
| 2015/0148668 A1* | 5/2015 | Stolka | A61B 5/0082 600/424 |

(Continued)

FOREIGN PATENT DOCUMENTS

| | | |
|---|---|---|
| JP | 2011-200533 A | 10/2011 |
| JP | 2014-221175 A | 11/2014 |

OTHER PUBLICATIONS

Lin et al., "HoloNeedle: Augmented-reality Guidance System for Needle Placement Investigating the Advantages of 3D Needle Shape Reconstruction," (Aug. 6, 2018), IEEE Robotics and Automation Letters. pp. 1-1. (Year: 2018).*

(Continued)

*Primary Examiner* — Joel Lamprecht
*Assistant Examiner* — Ashish S Jasani
(74) *Attorney, Agent, or Firm* — Studebaker & Brackett PC

(57) ABSTRACT

An ultrasound diagnostic apparatus includes a head-mounted display that is mounted on a head of a user and has a camera unit configured to acquire a view image obtained by imaging a field of view in front of the user, and a puncture needle length calculation unit (46) that, in a case where at least a part of the puncture needle is imaged by the camera unit, recognizes the puncture needle by performing image analysis on the view image, and calculates a length of the puncture needle in the view image.

13 Claims, 13 Drawing Sheets

(56) References Cited

U.S. PATENT DOCUMENTS

| | | | | |
|---|---|---|---|---|
| 2016/0119529 A1* | 4/2016 | Stolka | ................... | A61B 8/466 |
| | | | | 348/211.1 |
| 2019/0056693 A1* | 2/2019 | Gelman | ................ | G06T 19/006 |
| 2022/0079675 A1* | 3/2022 | Lang | ..................... | G02B 30/52 |

OTHER PUBLICATIONS

Vaughan et al., "Real-time length measurement of epidural Tuohy needle during insertion", (Jul. 3, 2013), IET Sci. Meas. Technol., 2013, vol. 7, Iss. 4, pp. 215-222 215. (Year: 2013).*
International Search Report issued in PCT/JP2019/044461; dated Jan. 21, 2020.
International Preliminary Report on Patentability and Written Opinion issued in PCT/JP2019/044461; dated Jun. 16, 2021.
Csurka et al. Visual Categorization with Bags of Keypoints, Proc. of ECCV Workshop on Statistical Learning in Computer Vision, pp. 59-74 (2004).
Krizhevsk et al. ImageNet Classification with Deep Convolutional Neural Networks, Advances in Neural Information Processing Systems 25, pp. 1106-1114 (2012).
An Office Action; "Notice of Reasons for Refusal," mailed by the Japanese Patent Office dated Nov. 22, 2022, which corresponds to Japanese Patent Application No. 2020-562903 and is related to U.S. Appl. No. 17/353,435; with English language translation.
An Office Action mailed by the Japanese Patent Office dated Jul. 12, 2022, which corresponds to Japanese Patent Application No. 2020-562903 and is related to U.S. Appl. No. 17/353,435.

* cited by examiner

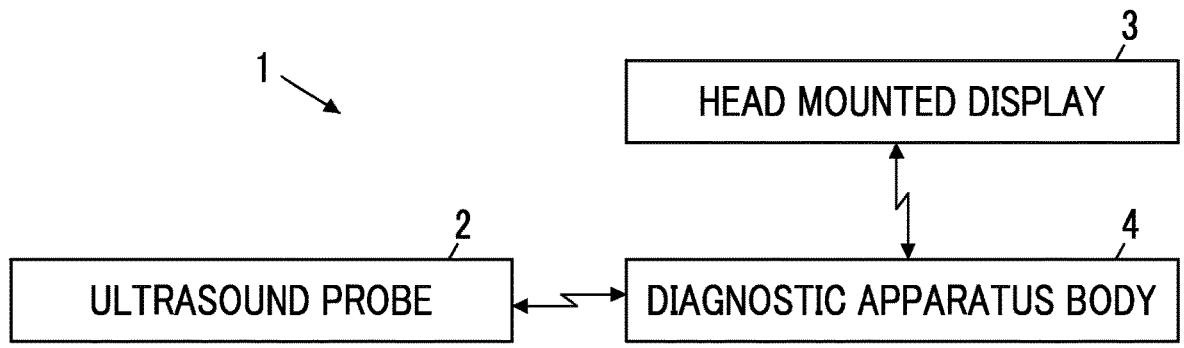
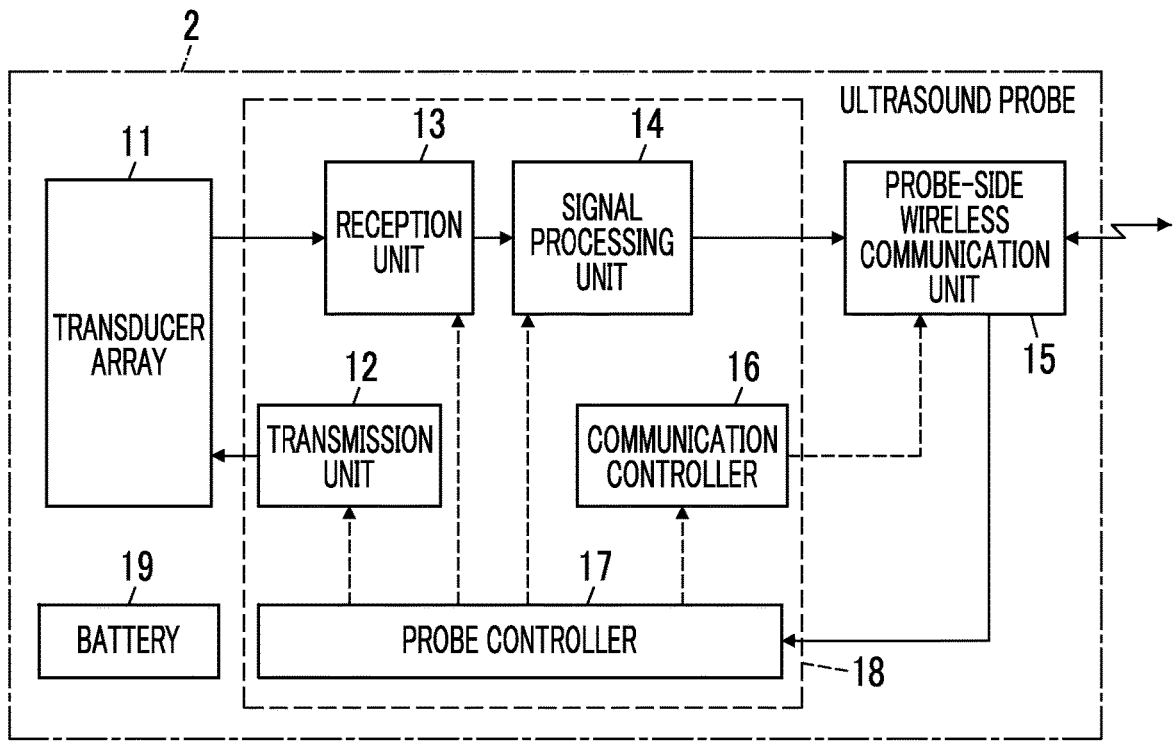
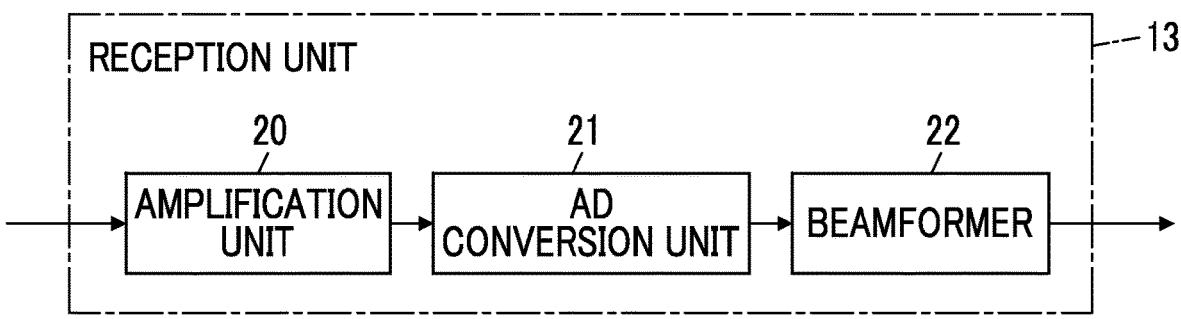

FIG. 12
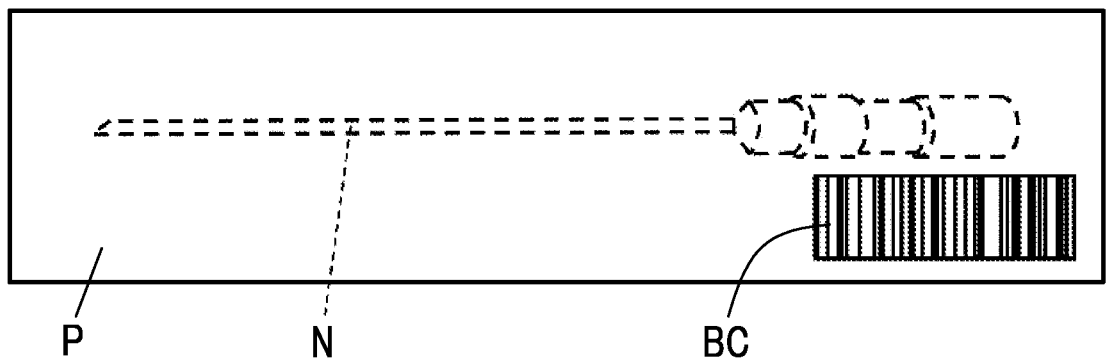
FIG. 13
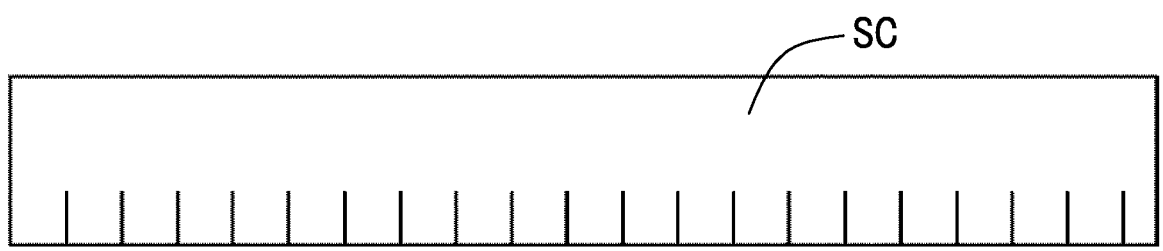
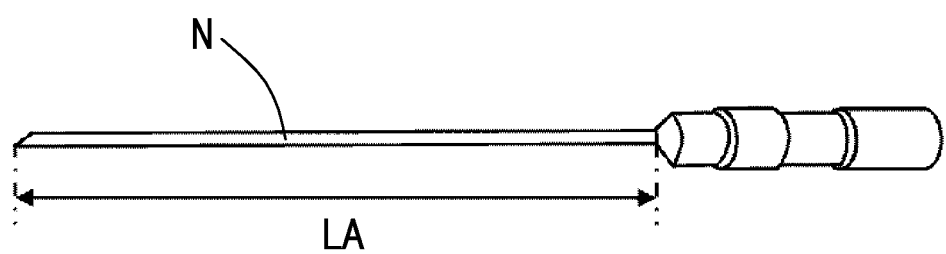

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2019/044461 filed on Nov. 13, 2019, which claims priority under 35 U.S.C. § 119(a) to Japanese Patent Application No. 2018-245545 filed on Dec. 27, 2018. Each of the above applications is hereby expressly incorporated by reference, in its entirety, into the present application.

BACKGROUND OF THE INVENTION

1. Field of the Invention

The present invention relates to an ultrasound diagnostic apparatus comprising a head-mounted display and a method of controlling an ultrasound diagnostic apparatus.

2. Description of the Related Art

Hitherto, as an apparatus that obtains an image inside a subject, an ultrasound diagnostic apparatus is known. In general, the ultrasound diagnostic apparatus comprises an ultrasound probe that comprises a transducer array in which a plurality of elements are arranged. In a state in which the ultrasound probe is brought into contact with a body surface of a subject, an ultrasonic beam is transmitted from the transducer array into the subject, and the transducer array receives an ultrasound echo from the subject to acquire element data. The ultrasound diagnostic apparatus electrically processes the obtained element data to generate an ultrasound image of a corresponding part of the subject.

Such an ultrasound diagnostic apparatus may be used to observe a puncture needle inserted into the subject in a case where the puncture needle is inserted into the subject. In this case, a user inserts the puncture needle into the subject while observing the puncture needle rendered in the ultrasound image by confirming the ultrasound image displayed on a monitor in a state in which the puncture needle is inserted into the subject while bringing the ultrasound probe into contact with the subject.

Here, usually, the monitor on which the ultrasound image is displayed is often disposed at a position away from the ultrasound probe, such as a bedside, and thus, the user needs to alternately move a line of sight between the puncture needle at hand and the ultrasound probe, and the monitor. To reduce the movement of the line of sight of the user, for example, an ultrasound diagnostic apparatus comprising a so-called head-mounted display as disclosed in JP2011-200533A has been developed. In the ultrasound diagnostic apparatus, an ultrasound image where a puncture needle is rendered is displayed on a display unit of the head-mounted display.

SUMMARY OF THE INVENTION

Incidentally, it is preferable that the user recognizes a length of a portion of the puncture needle inserted into the subject from a viewpoint of safety in inserting the puncture needle into the subject. In the ultrasound diagnostic apparatus of JP2011-200533A, although the user can confirm the puncture needle on the ultrasound image while reducing the movement of the line of sight by viewing the display unit of the head-mounted display, the user hardly exactly recognizes the length of the portion of the puncture needle inserted into the subject merely by confirming the puncture needle on the ultrasound image. To exactly recognize the length of the portion of the puncture needle inserted into the subject, for example, although a measurement of the length of the puncture needle on the ultrasound image is exemplified, usually, the measurement of the length on the ultrasound image is often performed manually by the user, and actually, the user hardly measures the length of the puncture needle on the ultrasound image in the middle of inserting the puncture needle into the subject, and also hardly measure an exact length.

The invention has been accomplished to solve such problems in the related art, and an object of the invention is to provide an ultrasound diagnostic apparatus and a method of controlling an ultrasound diagnostic apparatus capable of allowing a user to exactly and simply recognize a length of a portion of a puncture needle inserted into a subject.

To achieve the above-described object, the invention provides an ultrasound diagnostic apparatus that renders a puncture needle inserted into a subject in an ultrasound image. The ultrasound diagnostic apparatus comprises a head-mounted display that is mounted on a head of a user and has a camera unit configured to acquire a view image obtained by imaging a field of view in front of the user, and a puncture needle length calculation unit that, in a case where at least a part of the puncture needle is imaged by the camera unit, recognizes the puncture needle by performing image analysis on the view image and calculates a length of the puncture needle in the view image.

It is preferable that the ultrasound diagnostic apparatus further comprises a total length acquisition unit that acquires an actual total length of the puncture needle not inserted into the subject, and an actual length estimation unit that acquires a correspondence relationship between the length of the puncture needle in the view image calculated by the puncture needle length calculation unit from the view image where the whole of the puncture needle not inserted into the subject is imaged and the actual total length of the puncture needle acquired by the total length acquisition unit, and estimates an actual length of the puncture needle imaged in the view image from the length of the puncture needle in the view image calculated by the puncture needle length calculation unit, based on the acquired correspondence relationship.

In this case, in a case where the whole of the puncture needle that has a plurality of grooves disposed at given intervals and is not inserted into the subject is imaged by the camera unit, the total length acquisition unit may acquire the actual total length of the puncture needle using the plurality of grooves.

Alternatively, in a case where a length information recording member on which length information representing the actual total length of the puncture needle is recorded is imaged by the camera unit, the total length acquisition unit may acquire the actual total length of the puncture needle by reading the length information recorded on the length information recording member.

Alternatively, in a case where the whole of the puncture needle not inserted into the subject and a scale for measuring a length are imaged in parallel with each other by the camera unit, the total length acquisition unit may acquire the actual total length of the puncture needle using the scale.

The actual length estimation unit may display the estimated actual length of the puncture needle on the ultrasound image in a superimposed manner.

It is preferable that the ultrasound diagnostic apparatus further comprises an insertion length estimation unit that, in a case where the puncture needle at least a part of which is inserted into the subject is imaged by the camera unit, estimates an actual length of a portion of the puncture needle inserted into the subject based on the actual total length of the puncture needle acquired by the total length acquisition unit and an actual length of an uninserted portion of the puncture needle, which is shown in the view image, estimated by the actual length estimation unit.

In this case, the insertion length estimation unit may display the estimated actual length of the portion of the puncture needle inserted into the subject on the ultrasound image in a superimposed manner.

It is preferable that the ultrasound diagnostic apparatus further comprises a distance calculation unit that, in a case where a target part of puncture and the puncture needle are rendered in the ultrasound image, recognizes the target part and the puncture needle by performing image analysis on the ultrasound image, and calculates a distance between the target part and a distal end portion of the puncture needle based on the target part and the actual length of the portion of the puncture needle inserted into the subject estimated by the insertion length estimation unit.

In this case, the distance calculation unit may display a value of the calculated distance between the target part and the distal end portion of the puncture needle on the ultrasound image in a superimposed manner.

The ultrasound diagnostic apparatus may further comprise a notification unit that, in a case where the distance calculated by the distance calculation unit is equal to or less than a given value, gives notification to the user.

The head-mounted display may have a display unit that displays the ultrasound image.

Alternatively, the ultrasound diagnostic apparatus may further comprise a display monitor that displays the ultrasound image.

The invention provides a method of controlling an ultrasound diagnostic apparatus that renders a puncture needle inserted into a subject in an ultrasound image. The method comprises acquiring a view image obtained by imaging a field of view in front of a user by a head-mounted display that is mounted on a head of the user and has a camera unit, and in a case where at least a part of the puncture needle is imaged by the camera unit, recognizing the puncture needle by performing image analysis on the view image, and calculating a length of the puncture needle in the view image.

According to the invention, since the ultrasound diagnostic apparatus comprises the head-mounted display that is mounted on the head of the user and has the camera unit configured to acquire the view image obtained by imaging the field of view in front of the user, and the puncture needle length calculation unit that, in a case where at least a part of the puncture needle is imaged by the camera unit, recognizes the puncture needle by performing image analysis on the view image and calculates the length of the puncture needle in the view image, the user can exactly and simply the length of the portion of the puncture needle inserted into the subject.

BRIEF DESCRIPTION OF THE DRAWINGS

FIG. 1 is a block diagram showing the configuration of an ultrasound diagnostic apparatus according to Embodiment 1 of the invention.

FIG. 2 is a block diagram showing the configuration of an ultrasound probe in Embodiment 1 of the invention.

FIG. 3 is a block diagram showing the configuration of a reception unit in Embodiment 1 of the invention.

FIG. 12 is a diagram schematically showing a packaging bag of a puncture needle having a barcode.

FIG. 13 is a diagram schematically showing a manner in which a scale and a puncture needle are disposed in parallel.

DESCRIPTION OF THE PREFERRED EMBODIMENTS

Figure 4:
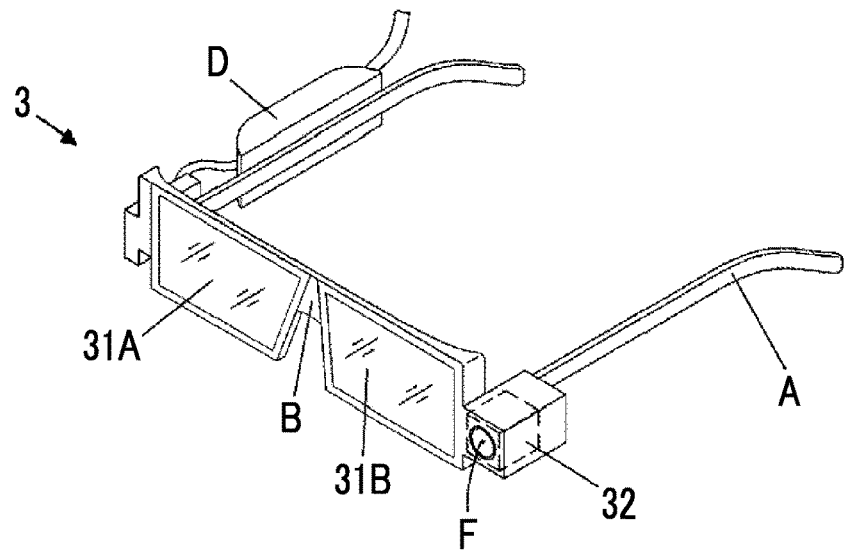
FIG. 4 is a diagram showing an example of a head-mounted display in Embodiment 1 of the invention.

Hereinafter, embodiments of the invention will be described referring to the accompanying drawings.

The description of components described below is provided based on a representative embodiment of the invention, but the invention is not limited to such an embodiment.

In the specification, a numerical range represented using "to" means a range including numerical values before and after "to" as a lower limit value and an upper limit value.

In the specification, the terms "perpendicular" and "parallel" include a range of an error allowed in the technical field to which the invention belongs. For example, the terms "perpendicular" and "parallel" mean a range less than ±10° with respect to strict perpendicular or parallel, and the error with respect to strict perpendicular or parallel is preferably equal to or less than 5°, and more preferably, equal to or less than 3°.

In the specification, the terms "same" and "identical" include an error range allowed in the technical field. In the specification, in a case of referring to "all", "any", "whole surface", or the like, the term includes an error range generally allowed in the technical field in addition to a case of 100%, and includes, for example, a case of equal to or more than 99%, a case of equal to or more than 95%, or a case of equal to or more than 90%.

Embodiment 1

FIG. 1 shows the configuration of an ultrasound diagnostic apparatus 1 according to Embodiment 1 of the invention. The ultrasound diagnostic apparatus 1 comprises an ultrasound probe 2, a head-mounted display 3, and a diagnostic apparatus body 4, and the ultrasound probe 2 and the head-mounted display 3 are connected to the diagnostic apparatus body 4 in a wireless state. The head-mounted display 3 is a display device that is mounted on a head of a user and is viewed by the user who mounts the head-mounted display 3, an ultrasound image and the like are transmitted from the diagnostic apparatus body 4 to the head-mounted display 3 in a wireless manner, and the transmitted ultrasound image and the like are displayed on the head-mounted display 3.

As shown in FIG. 2, the ultrasound probe 2 comprises a transducer array 11, and a transmission unit 12 and a reception unit 13 are connected to the transducer array 11. A signal processing unit 14 and a probe-side wireless communication unit 15 are sequentially connected to the reception unit 13. A communication controller 16 is connected to the probe-side wireless communication unit 15. A probe controller 17 is connected to the transmission unit 12, the reception unit 13, the signal processing unit 14, the probe-side wireless communication unit 15, and the communication controller 16, and the transmission unit 12, the reception unit 13, the signal processing unit 14, the communication controller 16, and the probe controller 17 constitute a probe processor 18. A battery 19 is incorporated in the ultrasound probe 2.

The transducer array 11 of the ultrasound probe 2 shown in FIG. 2 has a plurality of transducers arranged in a one-dimensional or two-dimensional manner. Each transducer transmits an ultrasonic wave in response to a drive signal supplied from the transmission unit 12, receives an ultrasound echo from a subject, and outputs a signal based on the ultrasound echo. Each transducer is constituted by forming electrodes at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 12 of the probe processor 18 includes, for example, a plurality of pulse generators, and adjusts a delay amount of each drive signal based on a transmission delay pattern selected in response to a control signal from the probe controller 17 such that the ultrasonic waves transmitted from a plurality of transducers of the transducer array 11 form an ultrasonic beam, and supplies the drive signals to a plurality of transducers. In this way, in a case where a pulsed or continuous-wave voltage is applied to the electrodes of each of a plurality of transducers of the transducer array 11, the piezoelectric body expands and contracts to generate a pulsed or continuous-wave ultrasonic wave from each of the transducers. An ultrasonic beam is formed from a combined wave of the ultrasonic waves.

The transmitted ultrasonic beam is reflected by, for example, a target, such as a part of the subject, and propagates toward the transducer array 11 of the ultrasound probe 2. The ultrasound echo propagating toward the transducer array 11 is received by each transducer constituting the transducer array 11. In this case, each transducer constituting the transducer array 11 expands and contracts with reception of the propagating ultrasound echo to generate an electrical signal, and outputs the electrical signal to the reception unit 13.

The reception unit 13 of the probe processor 18 performs processing on a signal output from the transducer array 11 in compliance with a control signal from the probe controller 17. As shown in FIG. 3, the reception unit 13 has a configuration in which an amplification unit 20, an analog-digital (AD) conversion unit 21, and a beamformer 22 are connected in series.

The amplification unit 20 amplifies the signal input from each transducer constituting the transducer array 11 and transmits the amplified signal to the AD conversion unit 21. The AD conversion unit 21 converts the signal transmitted from the amplification unit 20 into digital data and transmits the converted data to the beamformer 22. The beamformer 22 executes so-called reception focus processing by giving a delay to each piece of data converted by the AD conversion unit 21 in compliance with a sound speed or a distribution of a sound speed based on a reception delay pattern selected in response to a control signal from the probe controller 17 and performing addition. With the reception focus processing, each piece of data converted by the AD conversion unit 21 is subjected to phasing addition, and a reception signal with a narrowed focus of the ultrasound echo is acquired.

The signal processing unit 14 of the probe processor 18 performs correction of attenuation on reception data generated by the reception unit 13 due to a distance depending on a depth of a reflection position of the ultrasonic wave, and then, executes envelope detection processing, thereby generating an ultrasound image signal that is tomographic image information regarding a tissue in the subject.

The probe-side wireless communication unit 15 of the ultrasound probe 2 includes an antenna that performs transmission and reception of radio waves, and modulates a carrier based on the ultrasound image signals generated in the signal processing unit 14 to generate transmission signals representing the ultrasound image signals. The probe-side wireless communication unit 15 supplies the transmission signals representing the ultrasound image signals generated in this manner to the antenna and transmits radio waves from the antenna, thereby sequentially the ultrasound image signals to the diagnostic apparatus body 4 in a wireless manner. As a modulation system of the carrier, for example, amplitude shift keying (ASK), phase shift keying (PSK), quadrature phase shift keying (QPSK), 16 quadrature amplitude modulation (16QAM), or the like is used. The probe-side wireless communication unit 15 receives instruction information and the like for instructing the operation of the ultrasound probe 2 from the diagnostic apparatus body 4 and inputs the received instruction information and the like to the probe controller 17.

The communication controller 16 of the probe processor 18 performs control such that the probe-side wireless communication unit 15 transmits the ultrasound image signals with transmission field intensity set by the probe controller 17.

The probe controller 17 of the probe processor 18 performs control of each unit of the ultrasound probe 2 based on a program stored in advance, and the instruction information and the like transmitted from the diagnostic apparatus body 4 in a wireless manner.

The battery 19 of the ultrasound probe 2 is incorporated in the ultrasound probe 2, and supplies electric power to each circuit of the ultrasound probe 2.

Although the probe processor 18 having the transmission unit 12, the reception unit 13, the signal processing unit 14, the communication controller 16, and the probe controller 17 is constituted of a central processing unit (CPU) and a control program causing the CPU to execute various kinds of processing, the probe processor 18 may be constituted using a field programmable gate array (FPGA), a digital signal processor (DSP), an application specific integrated circuit (ASIC), or other integrated circuits (ICs) or may be constituted by combining the IC circuits. The transmission unit 12, the reception unit 13, the signal processing unit 14, the communication controller 16, and the probe controller 17 can also be constituted to be partially or wholly integrated into one CPU or the like.

The head-mounted display 3 is a display device that is mounted on the head of the user and is viewed by the user who mounts the head-mounted display 3, and as shown in FIG. 4, has a shape of so-called spectacles. The head-mounted display 3 comprises two display units 31A and 31B, and the two display units 31A and 31B are connected by a bridge portion B, and temple portions A are connected to end portions of the two display units 31A and 31B, respectively. For example, the bridge portion B is placed and fixed on a nose of the user, and the two temple portions A are placed and fixed on both ears of the user, whereby the head-mounted display 3 is fixed to the head of the subject. In this case, the two display units 31A and 31B face right and left eyes of the user, respectively.

A camera unit 32 that has an imaging lens F disposed on a front surface is attached to a connection portion of the left display unit 31B and the temple portion A. An accommodation portion D where various circuits necessary for the operation of the head-mounted display 3, a battery, and the like are accommodated is disposed in the temple portion A connected to the right display unit 31A.

Figure 5:
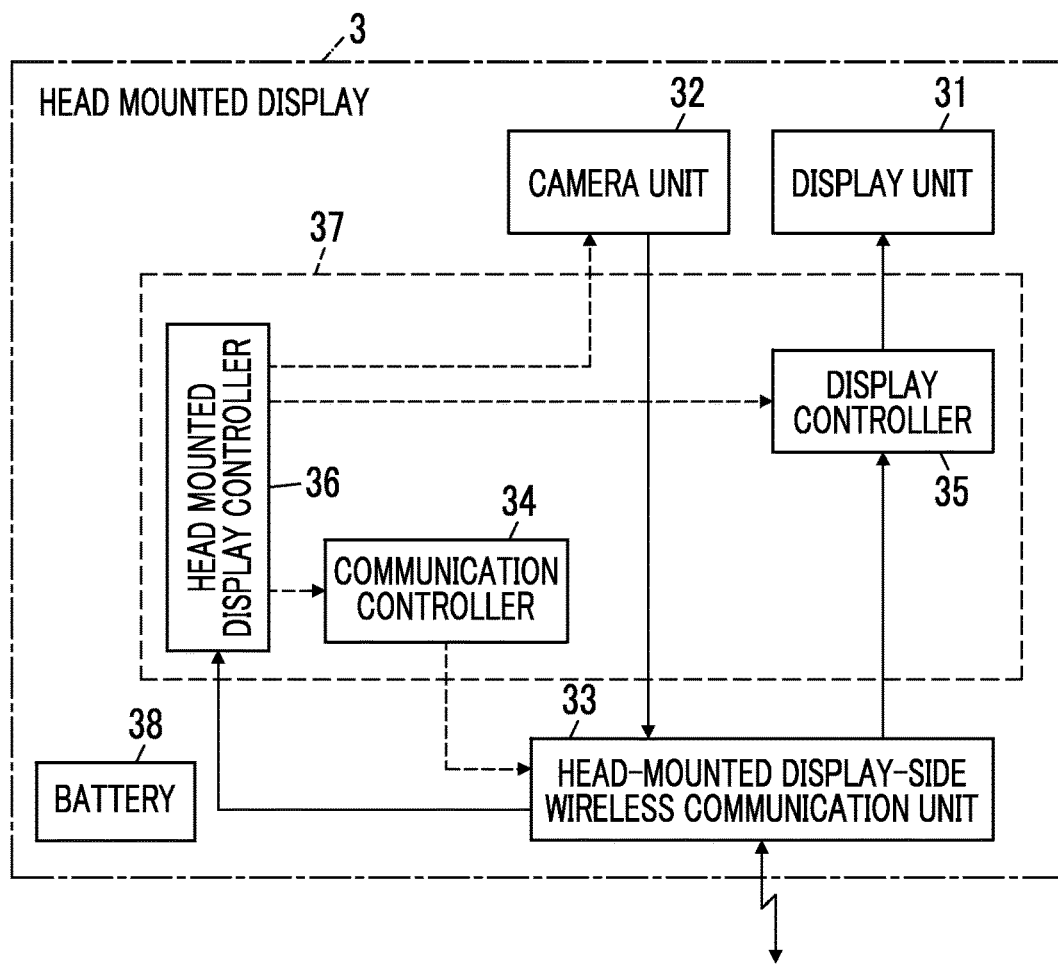
FIG. 5 is a block diagram showing the configuration of the head-mounted display in Embodiment 1 of the invention.

FIG. 5 shows the configuration of the head-mounted display 3. The head-mounted display 3 has a head-mounted display-side wireless communication unit 33, and the camera unit 32, a communication controller 34, and a display controller 35 are connected to the head-mounted display-side wireless communication unit 33. A display unit 31 is connected to the display controller 35. A head-mounted display controller 36 is connected to the camera unit 32, the head-mounted display-side wireless communication unit 33, the communication controller 34, and the display controller 35.

For description, the two display units 31A and 31B in FIG. 4 are collectively referred to as the display unit 31.

The communication controller 34, the display controller 35, and the head-mounted display controller 36 constitute a head-mounted display processor 37. A battery 38 is incorporated in the head-mounted display 3. The head-mounted display-side wireless communication unit 33, the head-mounted display processor 37, and the battery 38 are accommodated in the accommodation portion D of the head-mounted display 3.

The camera unit 32 of the head-mounted display 3 generates a view image obtained by imaging a field of view in front of the user through the imaging lens F. Though not shown, the camera unit 32 incorporates an image sensor that images the field of view in front of the user through the imaging lens F to acquire a view image signal as an analog signal, an analog signal processing circuit that amplifies the view image signal acquired by the image sensor to convert the view image signal to a digital signal, and a digital signal processing circuit that performs various kinds of correction, such as gain correction, on the converted digital signal to generate a view image.

The analog signal processing circuit and the digital signal processing circuit can also be incorporated in the head-mounted display processor 37.

Like the probe-side wireless communication unit 15 of the ultrasound probe 2, the head-mounted display-side wireless communication unit 33 of the head-mounted display 3 includes an antenna that performs transmission and reception of radio waves, and transmits the view image generated by the camera unit 32 to the diagnostic apparatus body 4. The head-mounted display-side wireless communication unit 33 receives the ultrasound image and the like transmitted from the diagnostic apparatus body 4 and transmits the received ultrasound image and the like to the display unit 31 through the display controller 35. The head-mounted display-side wireless communication unit 33 receives the instruction information and the like for instructing the operation of the head-mounted display 3 from the diagnostic apparatus body 4 and outputs the received instruction information and the like to the head-mounted display controller 36.

The display unit 31 of the head-mounted display 3 has transmittance to secure the field of view of the user in a state in which the user mounts the head-mounted display 3. The display unit 31 is a display that displays the ultrasound image and the like. The display unit 31 has such a configuration, and can thus display the ultrasound image and the like transmitted from the diagnostic apparatus body 4, for example.

The display controller 35 of the head-mounted display processor 37 executes predetermined processing on the ultrasound image and the like transmitted from the diagnostic apparatus body 4 and displays the ultrasound image and the like on the display unit 31 under the control of the head-mounted display controller 36.

The communication controller 34 of the head-mounted display processor 37 performs control such that the head-mounted display-side wireless communication unit 33 transmits the view image and receives the ultrasound image and the like with transmission and reception field intensity set by the head-mounted display controller 36.

The head-mounted display controller 36 of the head-mounted display processor 37 performs control of each unit of the head-mounted display 3 based on a program stored in advance, and the instruction information and the like transmitted from the diagnostic apparatus body 4 in a wireless manner.

The battery 38 of the head-mounted display 3 is incorporated in the head-mounted display 3, and supplies electric power to each circuit of the head-mounted display 3.

Although the head-mounted display processor 37 having the communication controller 34, the display controller 35, and the head-mounted display controller 36 is constituted of a CPU and a control program causing the CPU to execute various kinds of processing, the head-mounted display processor 37 may be constituted using an FPGA, a DSP, an ASIC, a graphics processing unit (GPU), or other ICs or may be constituted by combining the ICs. The communication controller 34, the display controller 35, and the head-mounted display controller 36 can also be constituted to be partially or wholly integrated into one CPU or the like.

Figure 6:
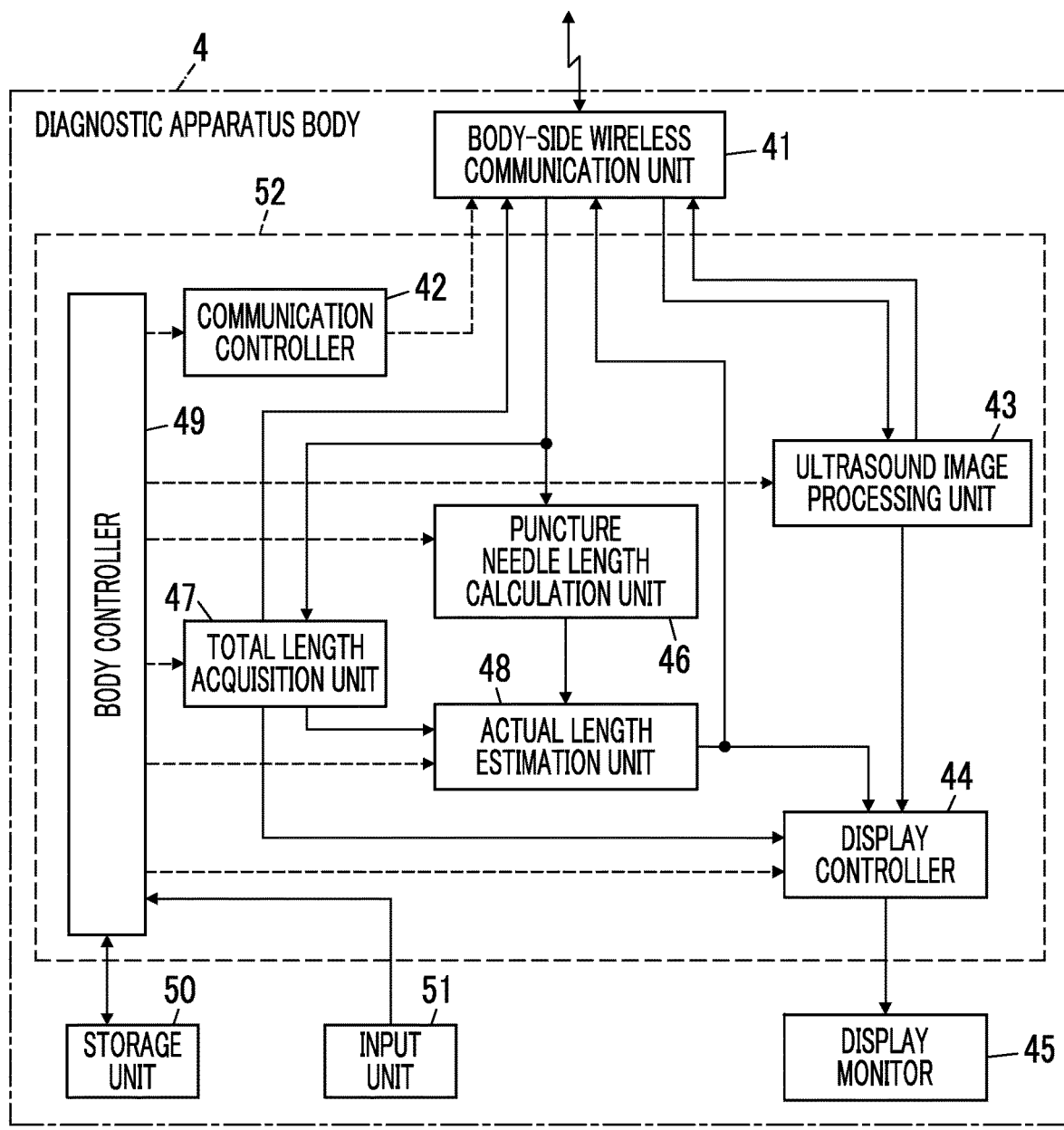
FIG. 6 is a block diagram showing the configuration of a diagnostic apparatus body in Embodiment 1 of the invention.

As shown in FIG. 6, the diagnostic apparatus body 4 has a body-side wireless communication unit 41, and a communication controller 42 is connected to the body-side wireless communication unit 41. An ultrasound image processing unit 43, a display controller 44, and a display monitor 45 are sequentially connected to the body-side wireless communication unit 41. A puncture needle length calculation unit 46 and a total length acquisition unit 47 are connected to the body-side wireless communication unit 41. An actual length estimation unit 48 is connected to the puncture needle length calculation unit 46, and the display controller 44 and the actual length estimation unit 48 are connected to the total length acquisition unit 47. The display controller 44 is connected to the actual length estimation unit 48. A body controller 49 is connected to the communication controller 42, the ultrasound image processing unit 43, the display controller 44, the puncture needle length calculation unit 46, the total length acquisition unit 47, and the actual length estimation unit 48, and a storage unit 50 and an input unit 51 are connected to the body controller 49. The body controller 49 and the storage unit 50 are connected to transfer information in two directions.

The communication controller 42, the ultrasound image processing unit 43, the display controller 44, the puncture needle length calculation unit 46, the total length acquisition unit 47, the actual length estimation unit 48, and the body controller 49 constitute a diagnostic apparatus body processor 52.

Like the probe-side wireless communication unit 15 of the ultrasound probe 2 and the head-mounted display-side wireless communication unit 33 of the head-mounted display 3, the body-side wireless communication unit 41 of the diagnostic apparatus body 4 includes an antenna that performs transmission and reception of radio waves, and transmits the instruction information and the like and receives the ultrasound image signal, the view image, and the like to and from the probe-side wireless communication unit 15 and the head-mounted display-side wireless communication unit 33 by wireless communication.

The ultrasound image processing unit 43 of the diagnostic apparatus body processor 52 receives the ultrasound image signal transmitted from the ultrasound probe 2, through the body-side wireless communication unit 41 and generates the ultrasound image based on the received ultrasound image signal. In this case, first, the ultrasound image processing unit 43 generates the ultrasound image by converting (raster-converting) the ultrasound image signal into an image signal compliant with a normal television signal scanning system. The ultrasound image processing unit 43 executes various kinds of necessary image processing, such as gradation processing, on the generated ultrasound image, and then, outputs the ultrasound image subjected to the image processing to the body-side wireless communication unit 41 and the display controller 44. Here, the ultrasound image output to the body-side wireless communication unit 41 is transmitted to the head-mounted display 3 by wireless communication.

The puncture needle length calculation unit 46 of the diagnostic apparatus body processor 52 receives the view image transmitted from the head-mounted display 3 through the body-side wireless communication unit 41, in a case where at least a part of a puncture needle inserted into the subject is shown in the received view image, recognizes the puncture needle by performing image analysis on the view image, and calculates the length of the puncture needle in the view image.

Figure 7:
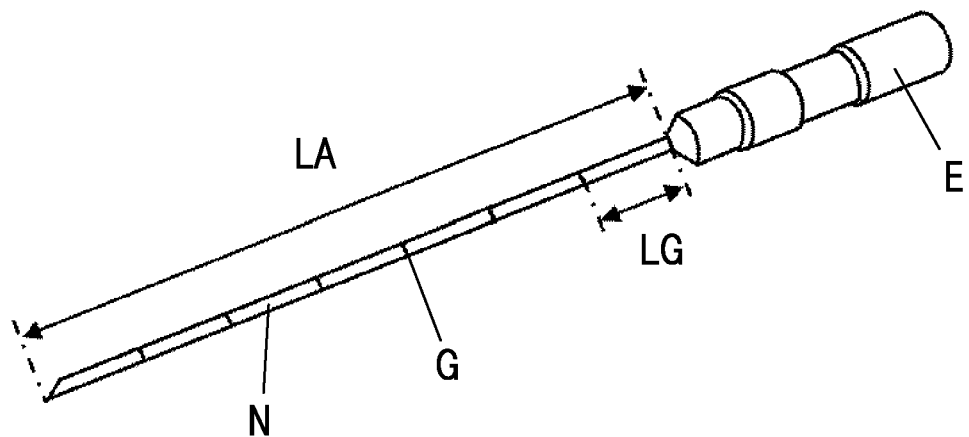
FIG. 7 is a diagram showing an example of a puncture needle.

Here, the puncture needle indicates, for example, a puncture needle shown in FIG. 7, and a puncture needle N has one end that has a sharp point to puncture the subject and the other end to which an attachment portion E for attachment of a cylinder or the like of a so-called syringe is connected. In general, such a puncture needle N is used for the purpose of collecting a sample from the inside of the subject, injecting a medicine into the subject, and the like.

In recognizing the puncture needle N shown in the view image, for example, the puncture needle length calculation unit 46 can store typical pattern data of the puncture needle as a template in advance, calculate a degree of similarity to pattern data while searching the inside of the view image based on the template, and consider that the puncture needle N is present at a place where the degree of similarity is equal to or greater than a threshold value and is the maximum.

For the calculation of the degree of similarity, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or deep learning described in Krizhevsk et al.: ImageNet Classification with Deep Convolutional Neural Networks, Advances in Neural Information Processing Systems 25, pp. 1106-1114 (2012) can be used.

The total length acquisition unit 47 of the diagnostic apparatus body processor 52 receives the view image transmitted from the head-mounted display 3, through the body-side wireless communication unit 41 and acquires an actual total length of the puncture needle N based on the received view image. For example, as shown in FIG. 7, in a case where a plurality of grooves G disposed at given intervals LG are formed in the puncture needle N, and the whole of the puncture needle N is shown in the view image, the total length acquisition unit 47 acquires an actual total length LA of the puncture needle N using the interval LG between a plurality of grooves G by performing image analysis on the view image. In this case, for example, the total length acquisition unit 47 can acquire the actual total length LA of the puncture needle N by storing an actual length of the interval LG between a plurality of grooves G in advance and referring to the stored actual length of the interval LG. A value of the interval LG between a plurality of grooves G can also be input by the user through the input unit 51.

Figure 8:
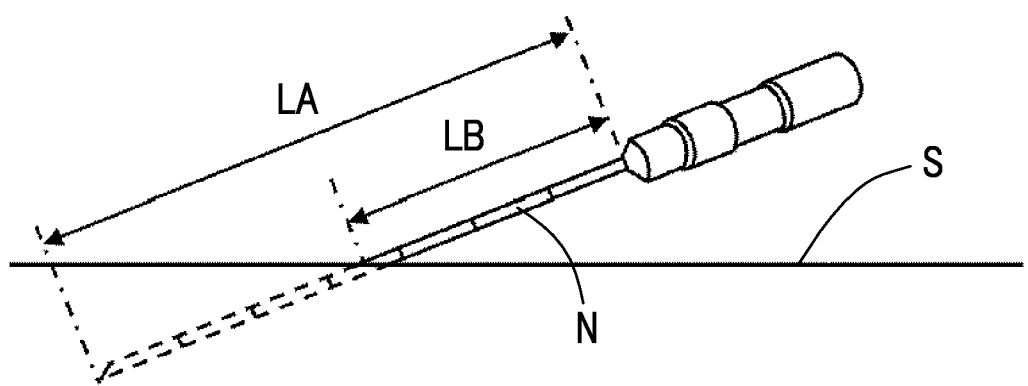
FIG. 8 is a diagram schematically showing the puncture needle inserted into a subject.

The actual length estimation unit 48 of the diagnostic apparatus body processor 52 acquires a correspondence relationship between the length of the puncture needle N in the view image calculated by the puncture needle length calculation unit 46 from the view image where the whole of the puncture needle N not inserted into the subject is imaged and the actual total length of the puncture needle N acquired by the total length acquisition unit 47, and estimates an actual length of the puncture needle N imaged in the view image based on the acquired correspondence relationship, from the length of the puncture needle N calculated by the puncture needle length calculation unit 46. For example, as shown in FIG. 8, in a case where the puncture needle N is inserted into a subject S and the puncture needle N is imaged by the camera unit 32 of the head-mounted display 3, an uninserted portion of the puncture needle N positioned outside the subject S is shown in the view image. In this case, the actual length estimation unit 48 estimates an actual length LB of the uninserted portion of the puncture needle N from the length of the puncture needle N in the view image calculated by the puncture needle length calculation unit 46 based on the actual total length LA of the puncture needle N.

The actual length estimation unit 48 sends a value of the estimated actual length of the puncture needle N to the body-side wireless communication unit 41 and the display controller 44. The value of the actual length of the puncture needle N sent to the body-side wireless communication unit 41 is transmitted to the head-mounted display 3 by wireless communication.

The display controller 44 of the diagnostic apparatus body processor 52 executes predetermined processing on the ultrasound image generated by the ultrasound image processing unit 43, the value of the actual length of the puncture needle N estimated by the actual length estimation unit 48, and the like and displays the ultrasound image and the estimated actual length of the puncture needle N on the body controller 49 under the control of the display monitor 45.

The display monitor 45 of the diagnostic apparatus body 4 displays an image under the control of the display controller 44, and includes, for example, a display device, such as a liquid crystal display (LCD) or an organic electroluminescence display (organic EL display).

The body controller 49 of the diagnostic apparatus body processor 52 performs control of each unit of the diagnostic apparatus body 4 based on a program stored in advance in the storage unit 50 or the like and a user's input operation through the input unit 51.

The communication controller 42 of the diagnostic apparatus body processor 52 performs control such that the body-side wireless communication unit 41 transmits and receives data with transmission and reception field intensity set by the body controller 49.

The input unit 51 of the diagnostic apparatus body 4 is provided for the user to perform an input operation, and can comprise a keyboard, a mouse, a trackball, a touch pad, a touch panel, and the like.

Although the diagnostic apparatus body processor 52 having the communication controller 42, the ultrasound image processing unit 43, the display controller 44, the puncture needle length calculation unit 46, the total length acquisition unit 47, the actual length estimation unit 48, and the body controller 49 is constituted of a CPU and a control program causing the CPU to execute various kinds of processing, the diagnostic apparatus body processor 52 may be constituted using an FPGA, a DSP, an ASIC, a GPU, or other ICs or may be constituted by combining the ICs. The communication controller 42, the ultrasound image processing unit 43, the display controller 44, the puncture needle length calculation unit 46, the total length acquisition unit 47, the actual length estimation unit 48, and the body controller 49 can also be constituted to be partially or wholly integrated into one CPU or the like.

Figure 9:
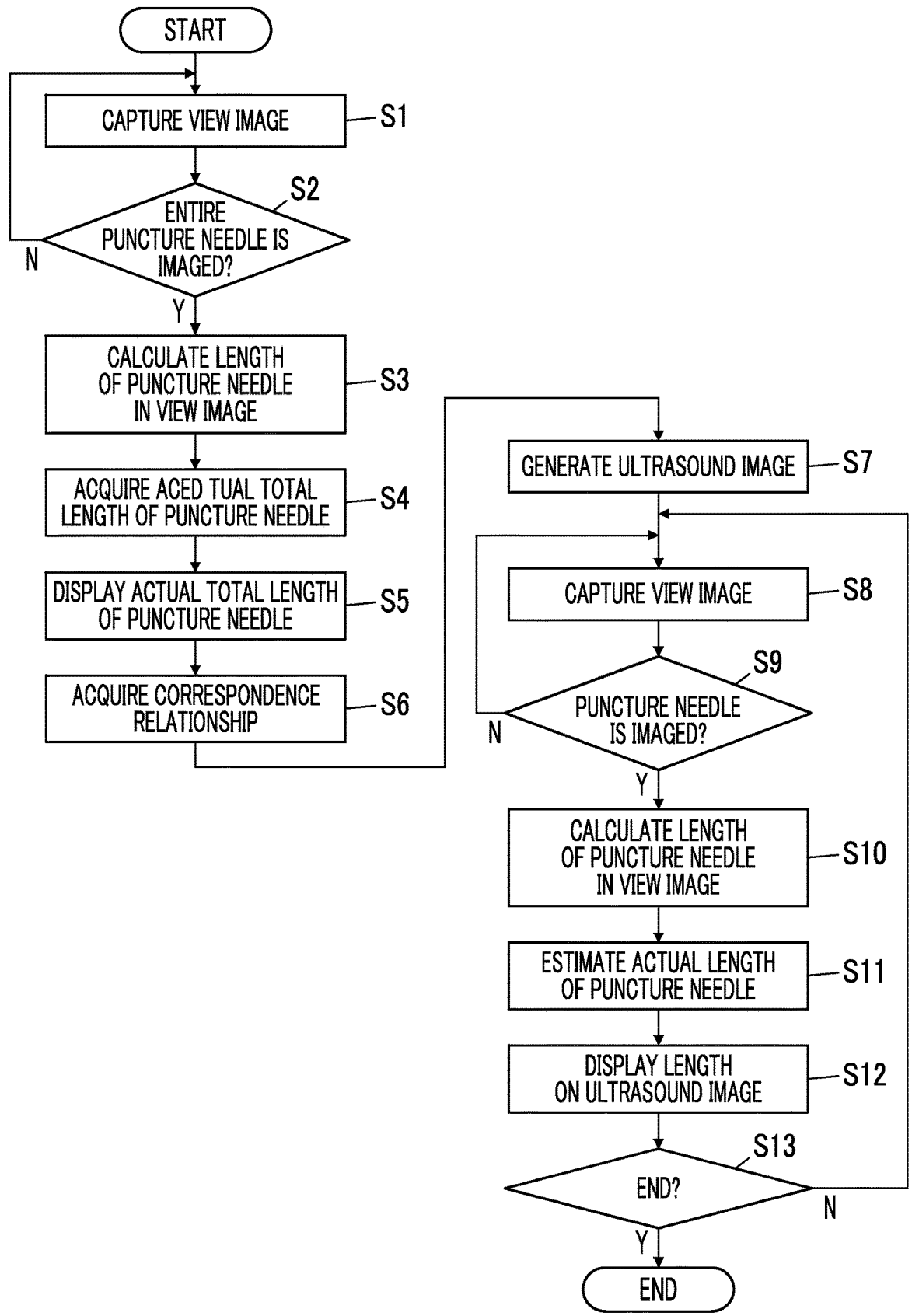
FIG. 9 is a flowchart showing the operation of the ultrasound diagnostic apparatus according to Embodiment 1 of the invention.

Next, the operation of the ultrasound diagnostic apparatus 1 according to Embodiment 1 of the invention will be described referring to a flowchart of FIG. 9.

First, in Step S1, the camera unit 32 of the head-mounted display 3 that is mounted on the head of the user generates a view image by imaging the field of view in front of the user.

In subsequent Step S2, determination is made whether or not the whole of the puncture needle N is imaged in Step S1, that is, whether or not the whole of the puncture needle N is shown in the view image generated in Step S1. In this case, for example, recognition processing of the puncture needle N is executed on the view image captured in Step S1, by the puncture needle length calculation unit 46 of the diagnostic apparatus body 4, in a case where the whole of the puncture needle N is recognized, determination is made that the whole of the puncture needle N is shown in the view image, and in a case where the whole of the puncture needle N is not recognized, determination is made that the whole of the puncture needle N is not shown in the view image.

In a case where determination is made that the whole of the puncture needle N is not imaged in Step S1, the process returns to Step S1, a view image is newly captured by the camera unit 32 of the head-mounted display 3, and the process progresses to Step S2. In this way, the processing of Steps S1 and S2 is repeated until determination is made in Step S2 that the whole of the puncture needle N is imaged in Step S1.

In a case where determination is made in Step S2 that the whole of the puncture needle N is imaged in Step S1, the process progresses to Step S3.

In Step S3, the total length of the puncture needle N in the view image is calculated by the puncture needle length calculation unit 46 based on the view image acquired in Step S1. In this case, the puncture needle length calculation unit 46 recognizes the whole of the puncture needle N shown in the view image by performing image analysis on the view image acquired in Step S1 and calculates the total length of the recognized puncture needle N on the view image.

In subsequent Step S4, the actual total length of the puncture needle N is acquired by the total length acquisition unit 47 of the diagnostic apparatus body 4. For example, as shown in FIG. 7, in a case where a plurality of grooves G disposed at the given interval LG are formed in the puncture needle N, and the whole of the puncture needle N is shown in the view image, the total length acquisition unit 47 acquires the actual total length LA of the puncture needle N using the interval LG between a plurality of grooves G by performing image analysis on the view image. In this case, for example, the total length acquisition unit 47 acquires the actual total length LA of the puncture needle N by storing the actual length of the interval LG between a plurality of grooves G in advance and referring to the stored actual length of the interval LG.

In Step S5, the actual total length LA of the puncture needle N acquired in Step S4 is displayed on the display unit 31 of the head-mounted display 3 and the display monitor 45 of the diagnostic apparatus body 4. Here, the actual total length LA of the puncture needle N acquired in Step S4 is continuously displayed on the display unit 31 of the head-mounted display 3 and the display monitor 45 of the diagnostic apparatus body 4 even thereafter. With this, the user can easily recognize the actual total length of the puncture needle N in use.

In Step S6, the correspondence relationship between the length of the puncture needle N on the view image calculated by the puncture needle length calculation unit 46 and the actual length of the puncture needle N imaged by the camera unit 32 of the head-mounted display 3 is acquired by the actual length estimation unit 48 of the diagnostic apparatus body 4 using the total length of the puncture needle N in the view image calculated in Step S3 and the actual total length of the puncture needle N acquired in Step S4. For example, the actual length estimation unit 48 can acquire, as the correspondence relationship, a ratio of the actual total length of the puncture needle N in the view image acquired in Step S4 to the total length of the puncture needle N in the view image calculated in Step S3. The actual length estimation unit 48 can estimate the actual length of the puncture needle N imaged in the view image from the length of the puncture needle N calculated by the puncture needle length calculation unit 46 using the acquired correspondence relationship.

In Step S7, an ultrasonic beam is transmitted from the transducer array 11 toward the inside of the subject S in a state in which the user brings the ultrasound probe 2 into contact with the subject S, and the transducer array 11 receives an ultrasound echo from the subject S to generate a reception signal. In a case where the reception signal is processed by the signal processing unit 14 of the ultrasound probe 2 and an ultrasound image signal is generated, an ultrasound image is generated by the ultrasound image processing unit 43 of the diagnostic apparatus body 4. The ultrasound image generated in this manner is displayed on the display unit 31 of the head-mounted display 3 and the display monitor 45 of the diagnostic apparatus body 4.

Even after Step S8, it is assumed that ultrasound images are sequentially generated and the generated ultrasound images are displayed on the display unit 31 of the head-mounted display 3 and the display monitor 45 of the diagnostic apparatus body 4. In a state in which the ultrasound images are sequentially generated, the user inserts the puncture needle N into the subject S while bringing the ultrasound probe 2 into contact with the subject S such that a place where the puncture needle N is inserted into the subject S is rendered in the ultrasound image.

Figure 10:
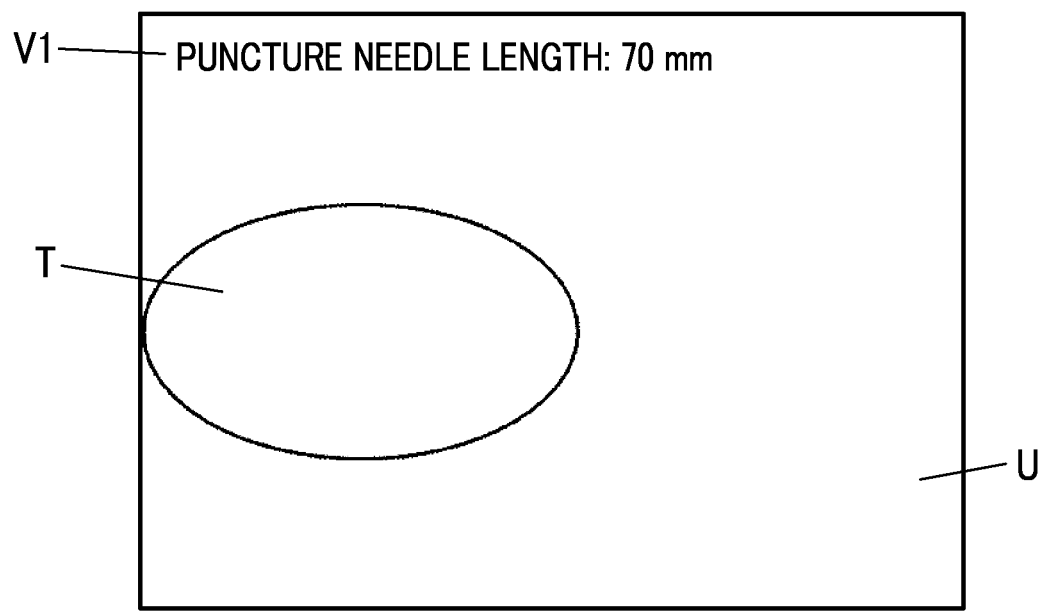
FIG. 10 is a diagram schematically showing an ultrasound image on which an acquired actual total length of the puncture needle is displayed.

In a case where the ultrasound image generated in Step S8 is displayed on the display unit 31 of the head-mounted display 3 and the display monitor 45 of the diagnostic apparatus body 4, the actual total length of the puncture needle N acquired in Step S4 is displayed on the display unit 31 of the head-mounted display 3 and the display monitor 45 of the diagnostic apparatus body 4 while being superimposed on the ultrasound image generated in Step S8. For example, in a state in which the puncture needle N is not inserted into the subject S, the actual total length of the puncture needle N acquired in Step S4 is superimposed on an ultrasound image U as a puncture needle length V1 as shown in FIG. 10. An indication that the puncture needle length V1 is 70 mm is superimposed on the ultrasound image U illustrated in FIG. 10, and a target part T to be a target of puncture is rendered.

In subsequent Step S8, as in Step S1, a view image is captured by the camera unit 32 of the head-mounted display 3.

In Step S9, determination is made whether or not at least a part of the puncture needle N is imaged in Step S8, that is, whether or not at least a part of the puncture needle N is shown in the view image captured in Step S8. In a case where determination is made in Step S9 that at least a part of the puncture needle N is not imaged in Step S8, the process returns to Step S8, a view image is newly captured by the camera unit 32 of the head-mounted display 3, and the process progresses to Step S9. In this way, the processing of Steps S8 and S9 is repeated until determination is made in Step S9 that at least a part of the puncture needle N is imaged in Step S8.

In a case where determination is made in Step S9 that at least a part of the puncture needle N is imaged in Step S8, the process progresses to Step S10.

In Step S10, the length of the puncture needle N in the view image captured in Step S7 is calculated by the puncture needle length calculation unit 46 of the diagnostic apparatus body 4. For example, as shown in FIG. 8, in a case where a part of the puncture needle N is inserted into the subject S, the length of an uninserted portion of the puncture needle N view image present outside the subject S is calculated.

In Step S11, the actual length of the puncture needle N imaged in the view image is estimated by the actual length estimation unit 48 of the diagnostic apparatus body 4. In this case, the actual length estimation unit 48 estimates the actual length of the puncture needle N imaged in the view image from the length of the puncture needle N calculated in Step S10 using the correspondence relationship between the total length of the puncture needle N in the view image and the actual total length of the puncture needle N obtained in Step S6. For example, as shown in FIG. 8, in a case where a part of the puncture needle N is inserted into the subject S, the actual length estimation unit 48 estimates the actual length LB of the uninserted portion of the puncture needle N based on the actual total length LA of the puncture needle N.

Figure 11:
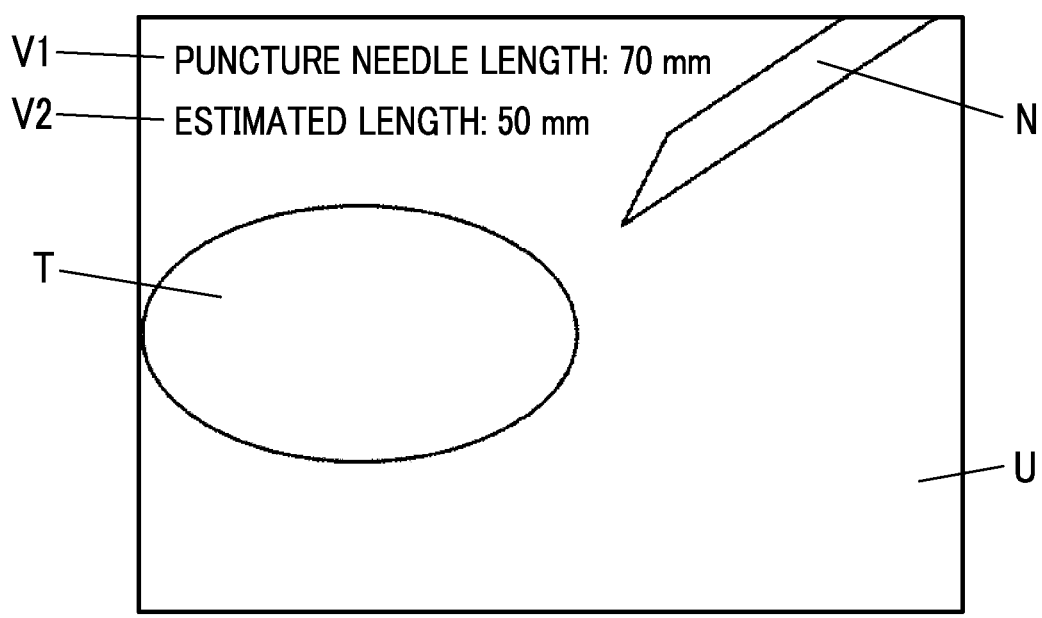
FIG. 11 is a diagram schematically showing an ultrasound image on which the acquired actual total length of the puncture needle and an estimated length of the puncture needle are displayed.

In subsequent Step S12, the actual length of the puncture needle N estimated in Step S11 by the actual length estimation unit 48 is displayed on the display unit 31 of the head-mounted display 3 and the display monitor 45 of the diagnostic apparatus body 4 while being superimposed on the ultrasound image U generated in Step S7. For example, in a case where a part of the puncture needle N is inserted into the subject S, as shown in FIG. 11, the actual length estimation unit 48 displays the actual length of the puncture needle N estimated in Step S11 as an estimated length V2 on the ultrasound image U in a superimposed manner. In the ultrasound image U illustrated in FIG. 10, an indication that the estimated length V2 is 50 mm is superimposed, and the puncture needle N and the target part T are rendered.

The user can easily recognize how much the puncture needle N is inserted into the subject S at present by confirming the length of the uninserted portion of the puncture needle N displayed on the display unit 31 of the head-mounted display 3 or the display monitor 45 of the diagnostic apparatus body 4 in this manner.

Finally, in Step S13, determination is performed whether or not to end the operation of the ultrasound diagnostic apparatus 1. Though not shown, for example, an end button for ending the operation of the ultrasound diagnostic apparatus 1 is displayed on the display unit 31 of the head-mounted display 3 and the display monitor 45 of the diagnostic apparatus body 4, in a case where the end button is pressed by the user through the input unit 51 or the like of the diagnostic apparatus body 4, determination is made to end the operation of the ultrasound diagnostic apparatus 1, and in a case where the end button is not pressed, determination is made to not end the operation of the ultrasound diagnostic apparatus 1.

In a case where determination is made in Step S13 to not end the operation of the ultrasound diagnostic apparatus 1, the processing of Steps S8 to S13 is executed again. In this way, the processing of Steps S8 to S13 is repeated until determination is made to end the operation of the ultrasound diagnostic apparatus 1. In a case where determination is made in Step S13 to end the operation of the ultrasound diagnostic apparatus 1, the operation of the ultrasound diagnostic apparatus 1 ends.

As described above, with the ultrasound diagnostic apparatus 1 according to Embodiment 1 of the invention, in a case where at least a part of the puncture needle N is imaged by the camera unit 32 of the head-mounted display 3, the length of the imaged puncture needle N is calculated by the puncture needle length calculation unit 46, the actual length of the puncture needle N is estimated by the actual length estimation unit 48 based on the calculated length of the puncture needle N, and the estimated actual length of the puncture needle N is displayed on the display unit 31 of the head-mounted display 3 and the display monitor 45 of the diagnostic apparatus body 4 while being superimposed on the ultrasound image U. Thus, the user can exactly and simply recognize the length of a portion of the puncture needle N inserted into the subject S.

In Embodiment 1, as shown in FIG. 7, although the puncture needle N that has a plurality of grooves G disposed at the given intervals LG has been illustrated, as a kind of the puncture needle N, a puncture needle further subject to so-called engraving for forming fine grooves over a given length from a distal end portion is known. For example, in a case where the whole of the engraved puncture needle N is imaged by the camera unit 32 of the head-mounted display 3, the total length acquisition unit 47 of the diagnostic apparatus body 4 can acquire the actual total length LA of the puncture needle N using the length of the engraved portion in addition to the interval LG between a plurality of grooves G.

Although an example where the total length acquisition unit 47 acquires the actual total length LA of the puncture needle N based on the interval LG between a plurality of grooves G formed in the puncture needle N has been described, a method of acquiring the actual total length LA of the puncture needle N is not limited thereto.

For example, as shown in FIG. 12, a barcode BC in which length information representing the actual total length LA of the puncture needle N is recorded is printed on a packaging bag P of the puncture needle N. In a case where the barcode BC is captured by the camera unit 32 of the head-mounted display 3, the total length acquisition unit 47 can acquire the actual total length LA of the puncture needle N by reading the length information recorded in the barcode BC shown in the view image. In this way, the total length acquisition unit 47 can also acquire the actual total length LA of the puncture needle N by reading length information recorded in a length information recording member, such as the barcode BC.

As shown in FIG. 13, in a case where the whole of the puncture needle N not inserted into the subject S and a scale SC for measuring a length are imaged in parallel with each other by the camera unit 32 of the head-mounted display 3, the total length acquisition unit 47 can calculate the actual total length LA of the puncture needle N based on the divisions of the scale.

In Embodiment 1, although an example where the ultrasound image U generated by the ultrasound image processing unit 43 of the diagnostic apparatus body 4 and the actual length of the puncture needle N estimated by the actual length estimation unit 48 are displayed on both the display unit 31 of the head-mounted display 3 and the display monitor 45 of the diagnostic apparatus body 4 has been described, the display may be performed on any one of the display unit 31 of the head-mounted display 3 and the display monitor 45 of the diagnostic apparatus body 4. Even in this case, the user can confirm the estimated actual length of the puncture needle N and exactly and simply recognize the length of the portion of the puncture needle N inserted into the subject S.

Although the ultrasound probe 2, the head-mounted display 3, and the diagnostic apparatus body 4 are connected by wireless communication, connection may be made in a wired manner instead of using wireless communication. For example, though not shown, the ultrasound probe 2 and the diagnostic apparatus body 4 can be connected in a wired manner, and the head-mounted display 3 and the diagnostic apparatus body 4 can be connected in a wired manner.

The shape of the head-mounted display 3 is not limited to the shape shown in FIG. 4 as long as the head-mounted display 3 comprises the display unit 31 that is visible by the user and the camera unit 32 that images the field of view in front of the user, and is mountable on the head of the user. For example, the head-mounted display 3 may comprise only one of the two display units 31A and 31B instead of comprising both the two display units 31A and 31B or may comprise only one display unit that faces both eyes of the user.

Although the diagnostic apparatus body 4 comprises the ultrasound image processing unit 43, the ultrasound probe 2, instead of the diagnostic apparatus body 4, may comprise the ultrasound image processing unit 43. In this case, the ultrasound image U is generated in the ultrasound probe 2, and the generated ultrasound image U is transmitted to the diagnostic apparatus body 4 through the probe-side wireless communication unit 15. The ultrasound image U transmitted to the diagnostic apparatus body 4 is input to the display controller 44 through the body-side wireless communication unit 41 of the diagnostic apparatus body 4 and is transmitted from the body-side wireless communication unit 41 to the head-mounted display 3. The ultrasound image U transmitted to the head-mounted display 3 is input to the display controller 35 through the head-mounted display-side wireless communication unit 33 of the head-mounted display 3. In this case, the ultrasound image U may be transmitted directly from the ultrasound probe 2 to the head-mounted display 3 without passing through the diagnostic apparatus body 4.

Embodiment 2

In Embodiment 1, although the actual length of the puncture needle N imaged by the camera unit 32 of the head-mounted display 3 is estimated by the actual length estimation unit 48 of the diagnostic apparatus body 4, the length of the portion of the puncture needle N inserted into the subject S can also be estimated based on an estimated length of the puncture needle N.

Figure 14:
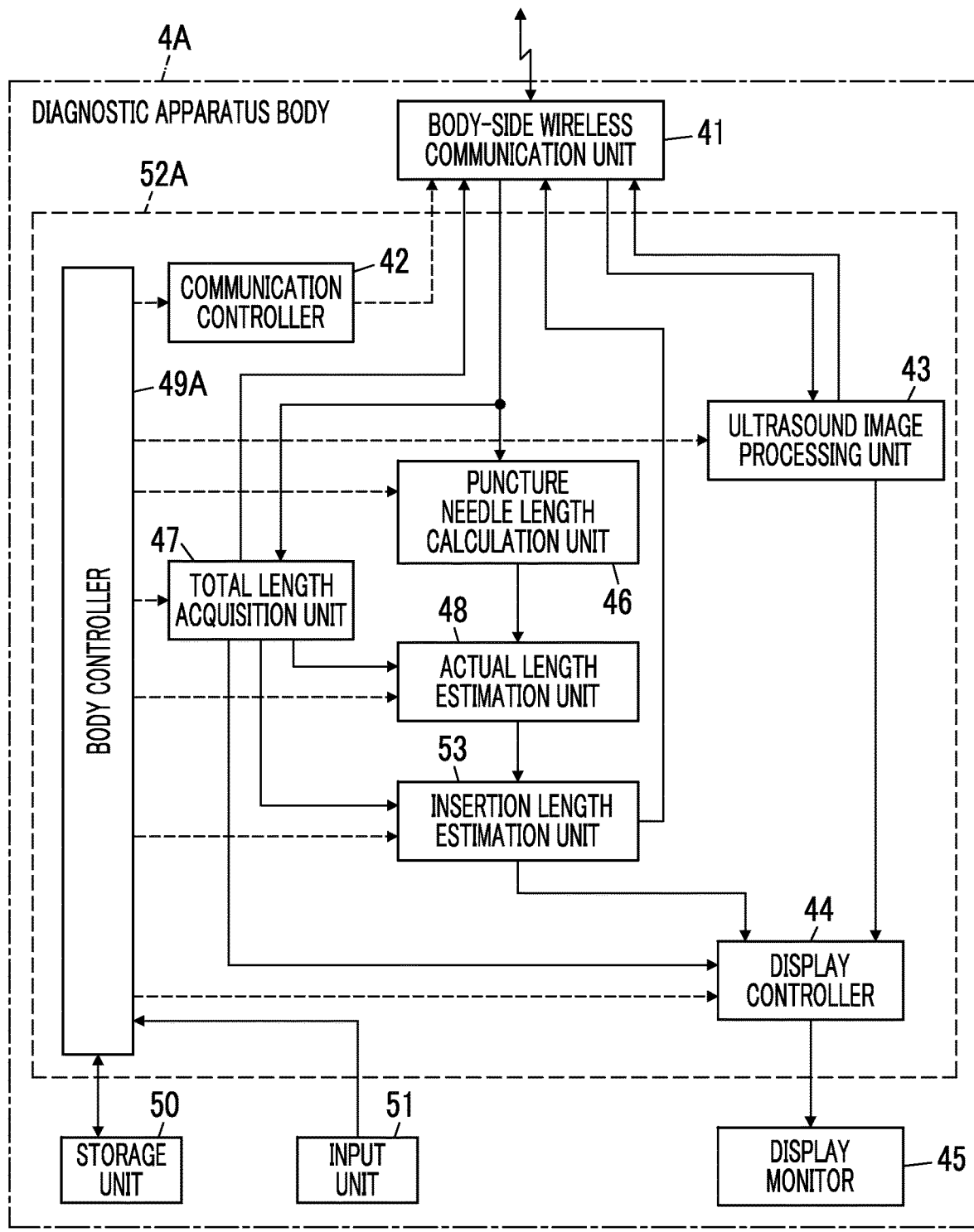
FIG. 14 is a block diagram showing the configuration of a diagnostic apparatus body in Embodiment 2 of the invention.

An ultrasound diagnostic apparatus according to Embodiment 2 has a configuration in which the ultrasound probe 2 and the head-mounted display 3 in Embodiment 1 are connected to a diagnostic apparatus body 4A shown in FIG. 14. The diagnostic apparatus body 4A of Embodiment 2 has a configuration in which a body controller 49A is provided instead of the body controller 49 in the diagnostic apparatus body 4 shown in FIG. 6, and an insertion length estimation unit 53 is added.

In the diagnostic apparatus body 4A, the insertion length estimation unit 53 is connected to the total length acquisition unit 47 and the actual length estimation unit 48, and the body-side wireless communication unit 41 and the display controller 44 are connected to the insertion length estimation unit 53. The body controller 49A is connected to the communication controller 42, the ultrasound image processing unit 43, the display controller 44, the puncture needle length calculation unit 46, the total length acquisition unit 47, the storage unit 50, the input unit 51, and the insertion length estimation unit 53.

The communication controller 42, the ultrasound image processing unit 43, the display controller 44, the puncture needle length calculation unit 46, the total length acquisition unit 47, the actual length estimation unit 48, the body controller 49A, and the insertion length estimation unit 53 constitute a diagnostic apparatus body processor 52A.

Figure 15:
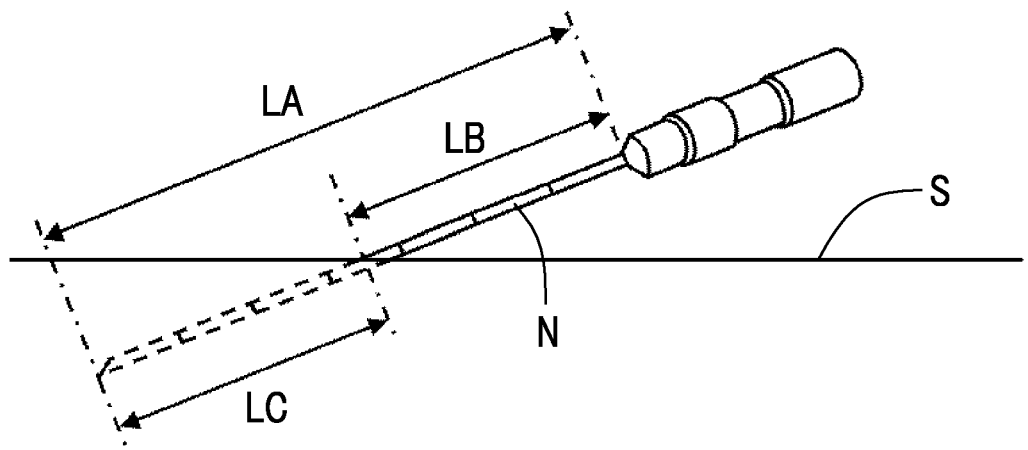
FIG. 15 is a diagram schematically showing a puncture needle inserted into a subject.

As shown in FIG. 15, in a case where the puncture needle N a part of which is inserted into the subject S is imaged by the camera unit 32 of the head-mounted display 3, the insertion length estimation unit 53 of the diagnostic apparatus body processor 52A estimates a length LC of a portion of the puncture needle N inserted into the subject S based on the actual total length LA of the puncture needle N acquired by the total length acquisition unit 47 and the actual length LB of the uninserted portion of the puncture needle N estimated by the actual length estimation unit 48. The insertion length estimation unit 53 sends a value of the estimated length LC to the body-side wireless communication unit 41 and the display controller 44, and displays the value of the estimated length LC on the display unit 31 of the head-mounted display 3 and the display monitor 45 of the diagnostic apparatus body 4A.

Figure 16:
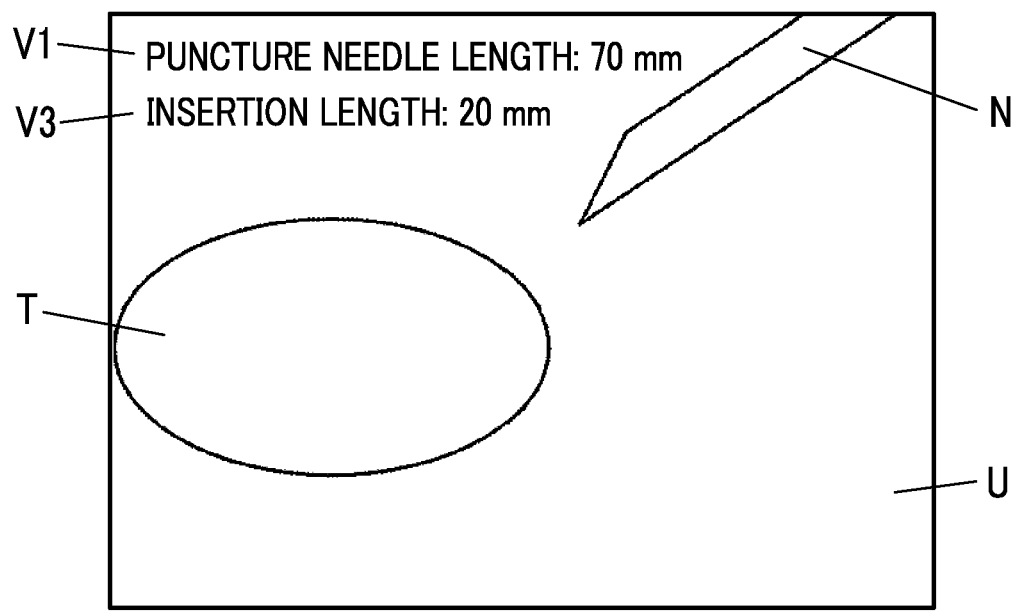
FIG. 16 is a diagram schematically showing an ultrasound image on which an acquired actual total length of the puncture needle and a length of a portion of the puncture needle inserted into the subject are displayed.

In this case, for example, as shown in FIG. 16, the insertion length estimation unit 53 displays the estimated length LC of the portion of the puncture needle N inserted into the subject S as an insertion length V3 on the ultrasound image U in a superimposed manner. An indication that the actual total length of the puncture needle N acquired by the total length acquisition unit 47, that is, the puncture needle length V1 is 70 mm, and an indication that the insertion length V3 is 20 mm are superimposed on the ultrasound image U illustrated in FIG. 16, and the puncture needle N inserted into the subject S and the target part T to be a target of puncture are rendered.

In this way, with the ultrasound diagnostic apparatus according to Embodiment 2, the length LC of the portion of the puncture needle N inserted into the subject S is estimated by the insertion length estimation unit 53, and the estimated length LC is displayed on the display unit 31 of the head-mounted display 3 and the display monitor 45 of the diagnostic apparatus body 4A while being superimposed on the ultrasound image U. Thus, the user can exactly and simply recognize the length of the portion of the puncture needle N inserted into the subject S.

In Embodiment 2, although the length LC of the portion of the puncture needle N inserted into the subject S estimated by the insertion length estimation unit 53 is displayed instead of displaying the actual length LB of the puncture needle N imaged in the view image estimated by the actual length estimation unit 48 of the diagnostic apparatus body 4A on the display unit 31 of the head-mounted display 3 and the display monitor 45 of the diagnostic apparatus body 4A, both the actual length LB of the puncture needle N and the length LC of the portion of the puncture needle N inserted into the subject S may be displayed on the display unit 31 of the head-mounted display 3 and the display monitor 45 of the diagnostic apparatus body 4A. Even in this case, the user can exactly and simply recognize the length of the portion of the puncture needle N inserted into the subject S.

Embodiment 3

In Embodiment 2, although the length LC of the portion of the puncture needle N inserted into the subject S is estimated by the insertion length estimation unit 53, a distance between the target part T to be a target of puncture and the distal end portion of the puncture needle N can be further calculated.

Figure 17:
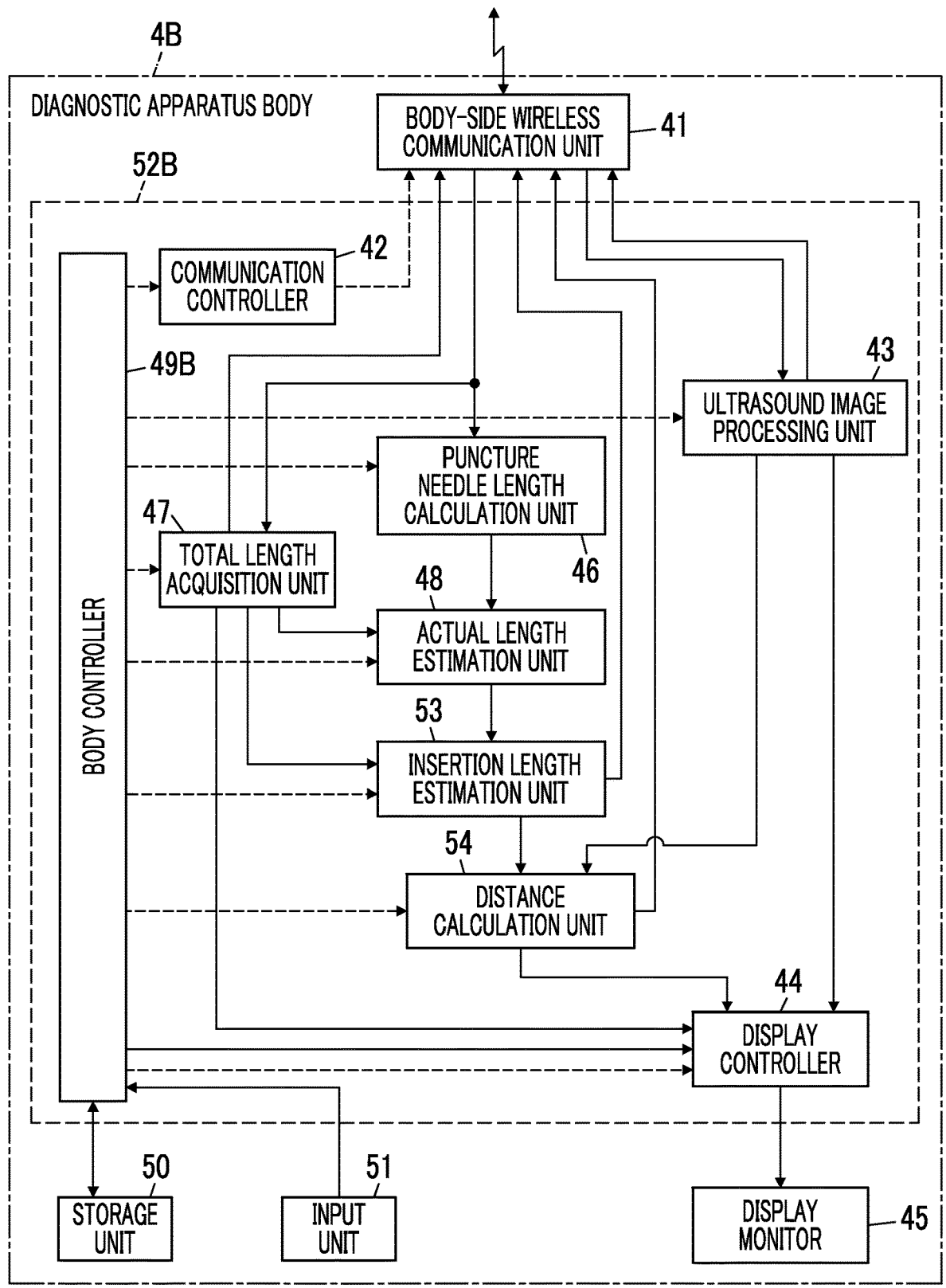
FIG. 17 is a block diagram showing the configuration of a diagnostic apparatus body in Embodiment 3 of the invention.

An ultrasound diagnostic apparatus according to Embodiment 3 has a configuration in which the ultrasound probe 2 and the head-mounted display 3 in Embodiment 1 are connected to a diagnostic apparatus body 4B shown in FIG. 17. The diagnostic apparatus body 4B of Embodiment 3 has a configuration in which a body controller 49B is provided instead of the body controller 49A in the diagnostic apparatus body 4A of Embodiment 2 shown in FIG. 14, and a distance calculation unit 54 is added.

In the diagnostic apparatus body 4B, the distance calculation unit 54 is connected to the ultrasound image processing unit 43 and the insertion length estimation unit 53, and the body-side wireless communication unit 41 and the display controller 44 are connected to the distance calculation unit 54. A body controller 49B is connected to the communication controller 42, the ultrasound image processing unit 43, the display controller 44, the puncture needle length calculation unit 46, the total length acquisition unit 47, the actual length estimation unit 48, the storage unit 50, the input unit 51, the insertion length estimation unit 53, and the distance calculation unit 54.

The communication controller 42, the ultrasound image processing unit 43, the display controller 44, the puncture needle length calculation unit 46, the total length acquisition unit 47, the actual length estimation unit 48, the body controller 49B, the insertion length estimation unit 53, and the distance calculation unit 54 constitute a diagnostic apparatus body processor 52B.

Figure 18:
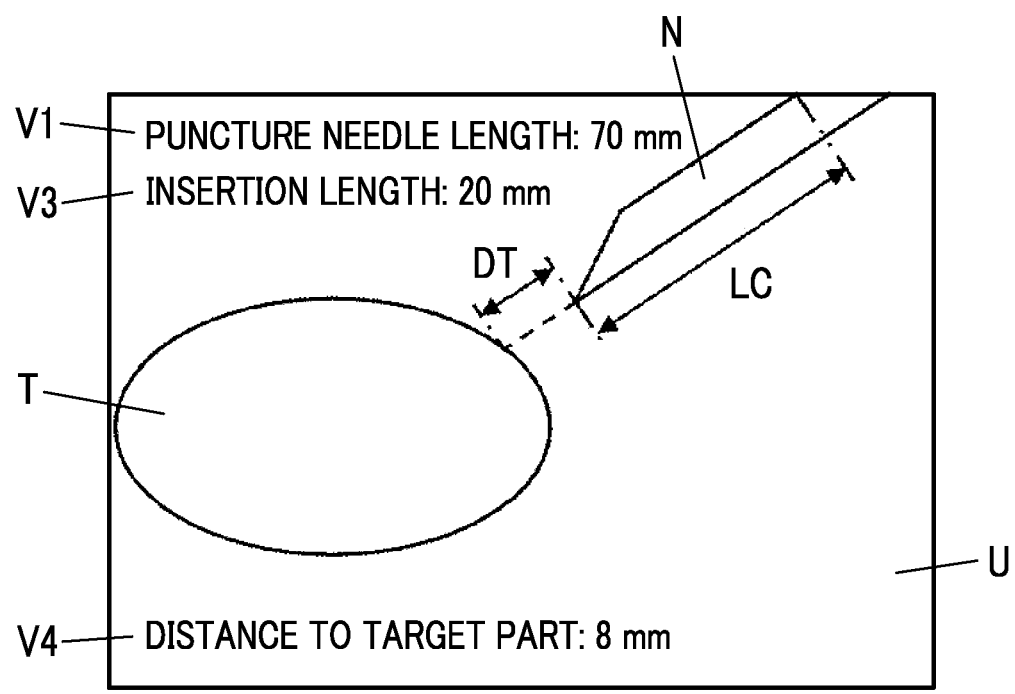
FIG. 18 is a diagram schematically showing an ultrasound image on which an acquired actual total length of a puncture needle, an estimated length of the puncture needle, and a distance between a target part and a distal end portion of the puncture needle.

As shown in FIG. 18, in a case where the target part T of puncture and the puncture needle N are rendered in the ultrasound image U, the distance calculation unit 54 of the diagnostic apparatus body processor 52B recognizes the target part T and the puncture needle N by performing image analysis on the ultrasound image U, and calculates a distance DT between the target part T and the distal end portion of the puncture needle N based on the target part T and the actual length LC of the portion of the puncture needle N inserted into the subject S estimated by the insertion length estimation unit 53. Here, the distance calculation unit 54 calculates, for example, a distance between the target part T and the distal end portion of the puncture needle N in an expansion direction of the puncture needle N as the distance DT between the target part T and the distal end portion of the puncture needle N.

The distance calculation unit 54 sends the distance DT between the target part T and the distal end portion of the puncture needle N calculated in this manner to the body-side wireless communication unit 41 and the display controller 44, and displays the distance DT on the display unit 31 of the head-mounted display 3 and the display monitor 45 of the diagnostic apparatus body 4B.

In this case, for example, as shown in FIG. 18, the distance calculation unit 54 displays the calculated distance DT between the target part T and the distal end portion of the puncture needle N as a distance V4 to the target part on the ultrasound image U in a superimposed manner. An indication that the actual total length of the puncture needle N acquired by the total length acquisition unit 47, that is, the puncture needle length V1 is 70 mm, an indication that the length of the portion of the puncture needle N inserted into the subject S estimated by the insertion length estimation unit 53, that is, the insertion length V3 is 20 mm, and an indication that the distance V4 to the target part is 8 mm are superimposed on the ultrasound image U illustrated in FIG. 18, and the puncture needle N inserted into the subject S and the target part T are rendered.

In this way, with the ultrasound diagnostic apparatus according to Embodiment 3, the distance DT between the target part T to be a target of puncture and the distal end portion of the puncture needle N is calculated by the distance calculation unit 54, and the calculated distance DT is displayed on the display unit 31 of the head-mounted display 3 and the display monitor 45 of the diagnostic apparatus body 4B. Thus, the user can exactly recognize a positional relationship of the puncture needle N with respect to the target part T.

Embodiment 4

In Embodiment 3, although the distance DT between the target part T and the distal end portion of the puncture needle N is calculated by the distance calculation unit 54, in a case where the calculated distance DT is short, that is, in a case where the distal end portion of the puncture needle N is close to the target part T, an indication can also be notified to the user.

Figure 19:
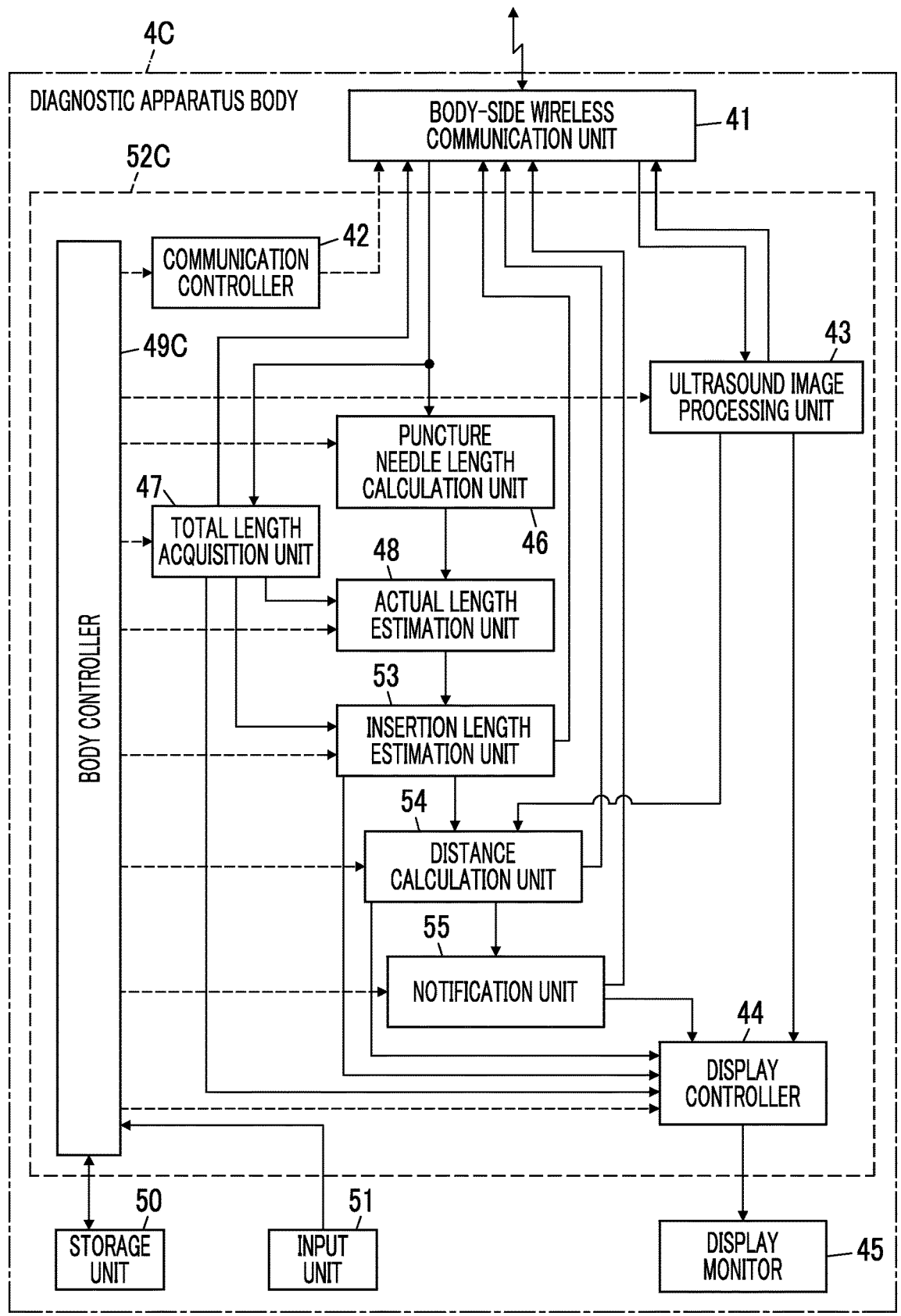
FIG. 19 is a block diagram showing the configuration of a diagnostic apparatus body in Embodiment 4 of the invention.

An ultrasound diagnostic apparatus according to Embodiment 4 has a configuration in which the ultrasound probe 2 and the head-mounted display 3 in Embodiment 1 are connected to a diagnostic apparatus body 4C shown in FIG. 19. The diagnostic apparatus body 4C of Embodiment 4 has a configuration in which a body controller 49C is provided instead of the body controller 49B in the diagnostic apparatus body 4B of Embodiment 3 shown in FIG. 17, and a notification unit 55 is added.

In the diagnostic apparatus body 4C, the notification unit 55 is connected to the distance calculation unit 54, and the body-side wireless communication unit 41 and the display controller 44 are connected to the notification unit 55. A body controller 49C is connected to the communication controller 42, the ultrasound image processing unit 43, the display controller 44, the puncture needle length calculation unit 46, the total length acquisition unit 47, the actual length estimation unit 48, the storage unit 50, the input unit 51, the insertion length estimation unit 53, the distance calculation unit 54, and the notification unit 55.

The communication controller 42, the ultrasound image processing unit 43, the display controller 44, the puncture needle length calculation unit 46, the total length acquisition unit 47, the actual length estimation unit 48, the body controller 49C, the insertion length estimation unit 53, the distance calculation unit 54, and the notification unit 55 constitute a diagnostic apparatus body processor 52C.

In a case where a value of the distance DT between the target part T and the distal end portion of the puncture needle N calculated by the distance calculation unit 54 is equal to or less than a given value, the notification unit 55 of the diagnostic apparatus body processor 52C notifies the user of an indication that the value of the distance DT is equal to or less than the given value. For example, though not shown, the notification unit 55 can give notification to the user by displaying text, an image, and the like representing an indication that the distal end portion of the puncture needle N is close to the target part T on the display unit 31 of the head-mounted display 3 and the display monitor 45 of the diagnostic apparatus body 4C while being superimposed on the ultrasound image U.

In this way, with the ultrasound diagnostic apparatus according to Embodiment 4, in a case where the distance DT between the target part T and the distal end portion of the puncture needle N is equal to or less than the given value, the notification unit 55 notifies the user of the indication that the distal end portion of the puncture needle N is close to the target part T. Thus, the user can exactly and clearly recognize a positional relationship of the puncture needle N with respect to the target part T.

Though not shown, in a case where a sound source unit, such as a speaker, is provided in the ultrasound probe 2, the head-mounted display 3, and the diagnostic apparatus body 4C, the notification unit 55 can also give notification to the user by notification sound, voice, or the like through the sound source unit. For example, in a case where the head-mounted display 3 comprises a vibration unit, such as a motor, that vibrates the head-mounted display 3, the notification unit 55 can also vibrate the head-mounted display 3 by the vibration unit to give notification to the user.

Embodiment 5

Although the ultrasound diagnostic apparatus 1 of Embodiment 1 has a configuration in which the ultrasound probe 2, the head-mounted display 3 are connected to the diagnostic apparatus body 4 by wireless communication, and the display monitor 45 and the input unit 51 are connected directly to the diagnostic apparatus body processor 52 of the diagnostic apparatus body 4, for example, the ultrasound probe 2, the head-mounted display 3, the display monitor 45, and the input unit 51 can also be connected to the diagnostic apparatus body processor 52 indirectly through a network.

Figure 20:
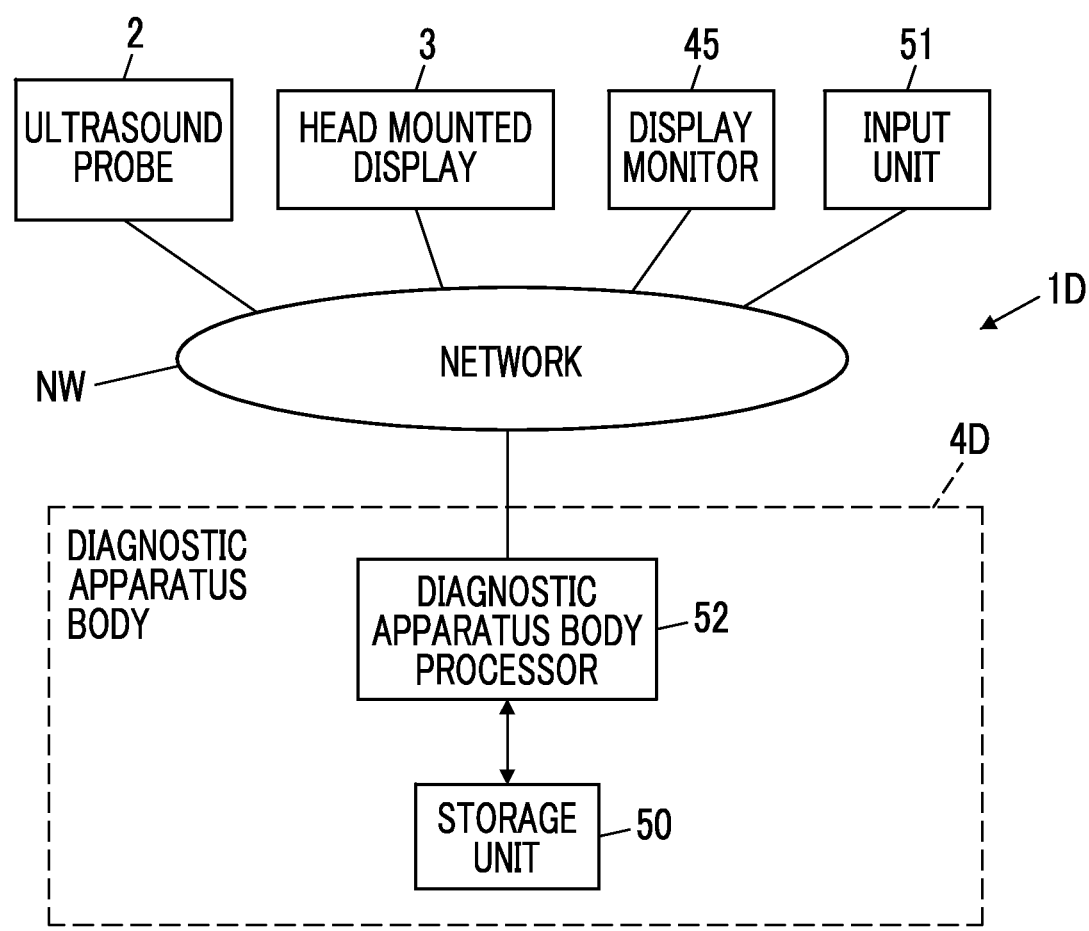
FIG. 20 is a block diagram showing the configuration of an ultrasound diagnostic apparatus according to Embodiment 5 of the invention.

As shown in FIG. 20, an ultrasound diagnostic apparatus 1D according to Embodiment 5 has a configuration in which the ultrasound probe 2, the head-mounted display 3, the display monitor 45, and the input unit 51 are connected to a diagnostic apparatus body 4D through a network NW. The diagnostic apparatus body 4D has a configuration in which the display monitor 45 and the input unit 51 in the diagnostic apparatus body 4 of Embodiment 1 shown in FIG. 6 are excluded, and is constituted of the diagnostic apparatus body processor 52 and the storage unit 50.

Even though the ultrasound diagnostic apparatus 1D has such a configuration, like the ultrasound diagnostic apparatus 1 of Embodiment 1, in a case where at least a part of the puncture needle N is imaged by the camera unit 32 of the head-mounted display 3, the length of the imaged puncture needle N is calculated by the puncture needle length calculation unit 46, the actual length of the puncture needle N is estimated by the actual length estimation unit 48 based on the calculated length of the puncture needle N, and the estimated actual length of the puncture needle N is displayed on the display unit 31 of the head-mounted display 3 and the display monitor 45 of the diagnostic apparatus body 4D while being superimposed on the ultrasound image U. For this reason, with the ultrasound diagnostic apparatus 1D, the user can exactly and simply recognize the length of the portion of the puncture needle N inserted into the subject S.

The ultrasound probe 2, the head-mounted display 3, the display monitor 45, and the input unit 51 are connected to the diagnostic apparatus body 4D through the network NW, and thus, the diagnostic apparatus body 4D can be used as a so-called remote server. With this, for example, the user can observe the inside of the subject S using the ultrasound image U by mounting the head-mounted display 3 on the head and preparing the ultrasound probe 2, the display monitor 45, and the input unit 51 at hand, and thus, it is possible to improve convenience in observing the inside of the subject S.

For example, in a case where a portable slim-type computer, called a tablet, is used as the display monitor 45 and the input unit 51, the user can more easily observe the inside of the subject S.

Although application of the aspect of Embodiment 5 to Embodiment 1 has been described, the aspect of Embodiment 5 can be similarly applied to Embodiment 2 to Embodiment 4.

EXPLANATION OF REFERENCES 1, 1A, 1B, 1C, 1D: ultrasound diagnostic apparatus
2: ultrasound probe
3: head-mounted display 4, 4A, 4B, 4C, 4D: diagnostic apparatus body
11: transducer array
12: transmission unit
13: reception unit
14: signal processing unit
15: probe-side wireless communication unit
16, 34, 42: communication controller
17: probe controller
18: probe processor
19, 38: battery
20: amplification unit
21: AD conversion unit
22: beamformer
31, 31A, 31B: display unit
32: camera unit
33: head-mounted display-side wireless communication unit
35, 44: display controller
36: head-mounted display controller
37: head-mounted display processor
41: body-side wireless communication unit
43: ultrasound image processing unit
45: display monitor
46: puncture needle length calculation unit
47: total length acquisition unit
48: actual length estimation unit
49, 49A, 49B, 49C: body controller
50: storage unit
51: input unit
52, 52A, 52B, 52C: diagnostic apparatus body processor
53: insertion length estimation unit
54: distance calculation unit
55: notification unit
A: temple portion
B: bridge portion
BC: barcode
D: accommodation portion
DT, V4: distance
E: attachment portion
F: imaging lens
G: groove
LA: total length
LB, LC: length
LG: interval
P: packaging bag
N: puncture needle
NW: network
S: subject
SC: scale
T: target part
U: ultrasound image
puncture needle length
V2: estimated length
V3: insertion length

What is claimed is:

1. An ultrasound diagnostic apparatus that renders a puncture needle configured to be inserted into a subject in an ultrasound image, the ultrasound diagnostic apparatus comprising:
a head-mounted display that is configured to be mounted on a head of a user and has a camera unit configured to acquire a view image obtained by imaging a field of view in front of the user; and
a processor configured to:
acquire an actual total length of the puncture needle not inserted into the subject by reading a length information recorded on a length information recording member from a first view image including the length information recording member acquired by the camera unit, where the length information represents the actual total length of the puncture needle and the length information recording member is provided separately from the puncture needle,
recognize the puncture needle by performing image analysis on a second view image including the whole of the puncture needle not inserted into the subject acquired by the camera unit to calculate a total length of the puncture needle on the second view image,
acquire a correspondence relationship between the actual total length of the puncture needle and the total length of the puncture needle on the second view image,
perform image analysis on a third view image including the puncture needle that is partly inserted into the subject acquired by the camera unit to calculate an image length of a part of the puncture needle that is not inserted into the subject in the third view image, and
estimate an actual length of an imaged portion of the puncture needle in the third view image based on the image length and the correspondence relationship.

2. The ultrasound diagnostic apparatus according to claim 1,
wherein, in a case where the whole of the puncture needle that has a plurality of grooves disposed at given intervals and is not inserted into the subject is imaged by the camera unit, the processor is configured to acquire the actual total length of the puncture needle using the plurality of grooves.

3. The ultrasound diagnostic apparatus according to claim 1,
wherein the processor is configured to display the estimated actual length of the puncture needle on the ultrasound image in a superimposed manner.

4. The ultrasound diagnostic apparatus according to claim 2,
wherein the processor is configured to display the estimated actual length of the puncture needle on the ultrasound image in a superimposed manner.

5. The ultrasonic diagnostic apparatus according to claim 1, wherein the processor is further configured to:
estimate an actual length of a portion of the puncture needle inserted into the subject based on the actual total length of the puncture needle and the actual length of the imaged portion of the puncture needle in the third view.

6. The ultrasonic diagnostic apparatus according to claim 2, wherein the processor is further configured to:
estimate an actual length of a portion of the puncture needle inserted into the subject based on the actual total length of the puncture needle and the actual length of the imaged portion of the puncture needle in the third view.

7. The ultrasound diagnostic apparatus according to claim 5,
wherein the processor is configured to display the estimated actual length of the portion of the puncture needle inserted into the subject on the ultrasound image in a superimposed manner.

8. The ultrasound diagnostic apparatus according to claim 5,
wherein, in a case where a target part of puncture and the puncture needle are rendered in the ultrasound image, the processor is configured to recognize the target part and the puncture needle by performing image analysis on the ultrasound image, and calculate a distance between the target part and a distal end portion of the puncture needle based on the target part and the estimated actual length of the portion of the puncture needle inserted into the subject.

9. The ultrasound diagnostic apparatus according to claim 8,
wherein the processor is configured to display a value of the calculated distance between the target part and the distal end portion of the puncture needle on the ultrasound image in a superimposed manner.

10. The ultrasound diagnostic apparatus according to claim 8,
wherein, in a case where the calculated distance is equal to or less than a given value, the processor is configured to give notification to the user.

11. The ultrasound diagnostic apparatus according to claim 1,
wherein the head-mounted display has a display unit configured to display the ultrasound image.

12. The ultrasound diagnostic apparatus according to claim 1, further comprising:
a display monitor configured to display the ultrasound image.

13. A method of controlling an ultrasound diagnostic apparatus that renders a puncture needle configured to be inserted into a subject in an ultrasound image, the method comprising:
acquiring a first view image obtained by imaging a field of view in front of a user including a length information recording member recording a length information by a head-mounted display that is configured to be mounted on a head of the user and has a camera unit, where the length information represents an actual total length of the puncture needle and the length information recording member is provided separately from the puncture needle;

acquiring the actual total length of the puncture needle not inserted into the subject by reading the length information recorded on the length information recording member from the first view image;

acquiring a second view image including the whole of the puncture needle not inserted into the subject by the head-mounted display;

recognizing the puncture needle by performing image analysis on the second view image to calculate a total length of the puncture needle on the second view image;

acquiring a correspondence relationship between the actual total length of the puncture needle and the total length of the puncture needle on the second view image;

acquiring a third view image including the puncture needle that is partly inserted into the subject by the head-mounted display;

performing image analysis in the third view image to calculate an image length of a part of the puncture needle that is not inserted into the subject in the third view image; and estimating an actual length of an imaged portion of the puncture needle in the third view image based on the image length and the correspondence relationship.

* * * * *